(12) United States Patent
Bito et al.

(10) Patent No.: US 10,836,802 B2
(45) Date of Patent: Nov. 17, 2020

US010836802B2

(54) CALCIUM REPORTER GENE

(71) Applicant: JAPAN SCIENCE AND TECHNOLOGY AGENCY, Kawaguchi-shi, Saitama (JP)

(72) Inventors: Haruhiko Bito, Tokyo (JP); Masatoshi Inoue, Tokyo (JP); Atsuya Takeuchi, Tokyo (JP); Junichi Nakai, Saitama (JP); Masamichi Ohkura, Saitama (JP)

(73) Assignee: JAPAN SCIENCE AND TECHNOLOGY AGENCY, Saitama (JP)

( * ) Notice: Subject to any disclaimer, the term of this patent is extended or adjusted under 35 U.S.C. 154(b) by 0 days.

(21) Appl. No.: 15/317,931

(22) PCT Filed: Jun. 8, 2015

(86) PCT No.: PCT/JP2015/002869
§ 371 (c)(1),
(2) Date: Dec. 9, 2016

(87) PCT Pub. No.: WO2015/190083
PCT Pub. Date: Dec. 17, 2015

(65) Prior Publication Data
US 2017/0152295 A1 Jun. 1, 2017

(30) Foreign Application Priority Data
Jun. 11, 2014 (JP) ................. 2014-120828

(51) Int. Cl.
| | |
|---|---|
| *C07K 19/00* | (2006.01) |
| *A61K 49/00* | (2006.01) |
| *C12Q 1/68* | (2018.01) |
| *C12Q 1/66* | (2006.01) |
| *C07K 14/47* | (2006.01) |
| *C07K 14/435* | (2006.01) |
| *C12N 15/00* | (2006.01) |
| *C12N 15/09* | (2006.01) |
| *C12N 5/10* | (2006.01) |
| *A01K 67/027* | (2006.01) |
| *C12Q 1/02* | (2006.01) |
| *C12N 9/12* | (2006.01) |
| *C12Q 1/6897* | (2018.01) |

(52) U.S. Cl.
CPC ............ *C07K 14/47* (2013.01); *A01K 67/027* (2013.01); *A61K 49/0045* (2013.01); *C07K 14/435* (2013.01); *C07K 19/00* (2013.01); *C12N 5/10* (2013.01); *C12N 9/12* (2013.01); *C12N 15/00* (2013.01); *C12N 15/09* (2013.01); *C12Q 1/02* (2013.01); *C12Q 1/66* (2013.01); *C12Q 1/6897* (2013.01); *C12Y 207/11017* (2013.01); *C07K 2319/60* (2013.01)

(58) Field of Classification Search
None
See application file for complete search history.

(56) References Cited

FOREIGN PATENT DOCUMENTS

| | | |
|---|---|---|
| JP | 2014-001161 A | 9/2014 |
| WO | 2000/071565 A2 | 11/2000 |

OTHER PUBLICATIONS

Pham, E., "Development of Protein-Based Tools to Image and Modulate Ca2+ Signaling", Thesis, University of Toronto, 2011 (Year: 2011).*
Li et al., "Sequence reversed peptide from CaMKK binds to calmodulin in reversible Ca2+-dependent manner", Biochem. Biophys. Res. Comm. 352:932-935, 2007 (Year: 2007).*
Okuno et al., "Evidence for the Existence of Ca2/Calmodulin-Dependent Protein Kinase IV Kinase Isoforms in Rat Brain", J. Biochem. 119:1176-1181, 1996 (Year: 1996).*
The Extended European Search Report and Written Opinion issued in related EP 15806391.7 dated Oct. 17, 2017.
Inoue et al., Rational design of a high-affinity, fast, red calcium indicator R-CaMP2. Nat Methods. Jan. 2015;12(1):64-70 plus supplementary data (13 pages total).
Matsushita and Nairn, Characterization of the Mechanism of Regulation of Ca2+/ Calmodulin-dependent Protein Kinase I by Calmodulin and by Ca2+/Calmodulin-dependent Protein Kinase Kinase. J Biol Chem. Aug. 21, 1998;273(34):21473-21481.
Ohkura et al., An Improved Genetically Encoded Red Fluorescent Ca2+ Indicator for Detecting Optically Evoked Action Potentials. PLoS One. 2012;7(7):e39933.
Sun et al., Fast GCaMPs for improved tracking of neuronal activity. Nat Commun. 2013;4:2170 (10 pages).
Tang et al., Fast kinetics of calcium signaling and sensor design. Curr Opin Chem Biol. Aug. 2015;27:90-97.
Chen et al., "Ultrasensitive fluorescent proteins for imaging neuronal activity", Nature. Jul. 18, 2013;499(7458):295-300. doi: 10.1038/nature12354.
Ohkura et al., "Genetically encoded green fluorescent Ca2+ indicators with improved detectability for neuronal Ca2+ signals", PLoS One. 2012;7(12):e51286. doi: 10.1371/journal.pone.0051286. Epub Dec. 11, 2012.

(Continued)

*Primary Examiner* — David Steadman
(74) *Attorney, Agent, or Firm* — Aciuty Law Group, PC; Michael A. Whittaker

(57) ABSTRACT

As a calcium indicator protein having an excellent fluorescent characteristic and calcium reactivity, there is provided DNA in which one of a nucleotide sequence derivative of a calmodulin-binding sequence (ckkap sequence) of calcium/calmodulin-dependent protein kinase kinase and a nucleotide sequence encoding a calcium-binding sequence (CaM sequence) of calmodulin is linked to a 5' end of a nucleotide sequence encoding a fluorescent protein, and the other nucleotide sequence is linked to a 3' end of the nucleotide sequence encoding the fluorescent protein. The calcium indicator protein encoded by this DNA, which based on the derivative of the ckkap sequence as a binding domain for the calcium-bound CaM sequence, exhibits a fluorescent characteristic and calcium reactivity superior to those of conventional calcium indicator proteins.

11 Claims, 12 Drawing Sheets
Specification includes a Sequence Listing.

(56) References Cited

OTHER PUBLICATIONS

Truong et al., "Fret-based in vivo Ca2+ imaging by a new calmodulin-GFP fusion molecule", Nat Struct Biol. Dec. 2001;8(12):1069-73.
Zhao et al., "An expanded palette of genetically encoded $Ca^{2+}$ indicators", Science. Sep. 30, 2011;333(6051):1888-91. doi: 10.1126/science.1208592. Epub Sep. 8, 2011.
International Search Report issued in PCT/JP2015/002869 dated Aug. 4, 2015 (4 pages).
Japanese Office Action dated May 8, 2018 in JP2016-527634 (4 pages).
Tallini et al., "Imaging cellular signals in the heat in vivo: Cardiac expression of the high-sginal CA2+ indicator GCaMP2", PNAS, 2006, 03(12):4753-4758.
Office Action issued in Chinese Patent Application No. 201580038699.3 dated Jun. 1, 2020—incl Engl lang transl. (15 pages total).
GenBank Sequence #NM_031338.1, Rattus norvegicus calcium/calmodulin-dependent protein kinase kinase 2, beta(Camkk2), mRNA. NCBI Feb. 1, 2014 (3 pages).

\* cited by examiner

FIG.1

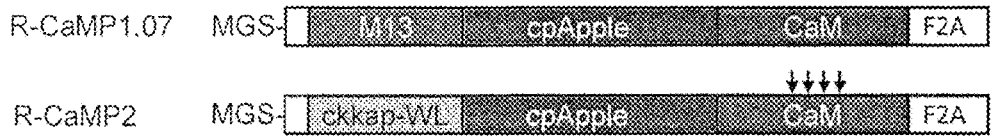

FIG.2A

```
ckkapα    VKLIPSWTTVILVKSMLRKRSFGNPF  (SEQ ID NO 4)
ckkapβ    VKHIPSLATVILVKTMIRKRSFGNPF  (SEQ ID NO 5)
ckkap-WL  VKLIPSLTTVILVKSMLRKRSFGNPF  (SEQ ID NO 6)
```

FIG.2B

```
ckkap-WL : V K L I P S L T T V I L V K S M L R K R S F G N P F  (SEQ ID NO 6)
ckkap-WL2: V K H I P S W T T V I L V K S M L R K R S F G N P F  (SEQ ID NO 15)
ckkap-WL3: V K H I P S L T T V I L V K S M L R K R S F G N P F  (SEQ ID NO 16)
ckkap-WL4: V K H I P S W A T V I L V K S M L R K R S F G N P F  (SEQ ID NO 17)
ckkap-WL5: V K L I P S L A T V I L V K S M L R K R S F G N P F  (SEQ ID NO 18)
ckkap-WL6: V K L I P S W A T V I L V K S M L R K R S F G N P F  (SEQ ID NO 19)
```

FIG.3

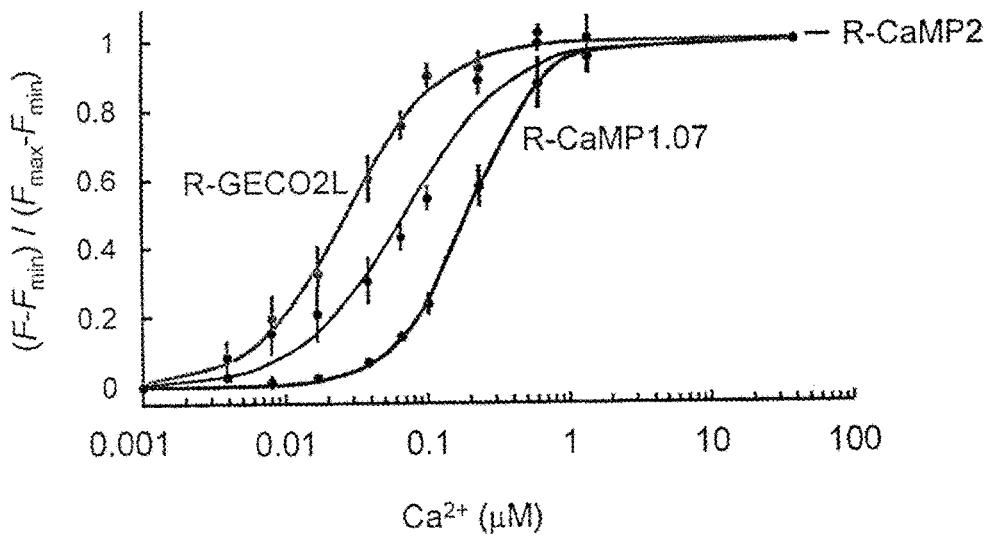

FIG. 15A
FIG. 15B
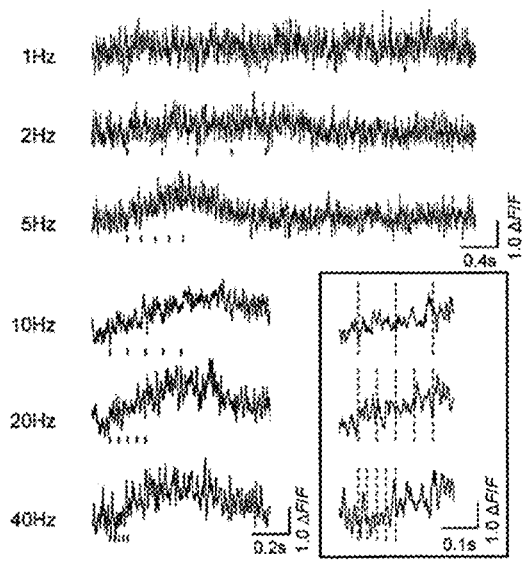
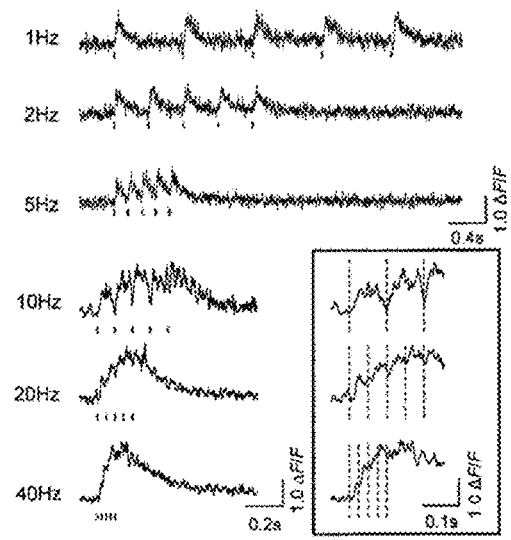

CALCIUM REPORTER GENE

CROSS-REFERENCE TO RELATED APPLICATIONS

The present invention is filed under 35 U.S.C. § 371 as the U.S. national phase of International Patent Application No. PCT/JP2015/002869, filed 8 Jun. 2015, which designated the U.S. and claims the benefit of priority to Japanese Patent Application No. 2014-120828, filed 11 Jun. 2014, each of which is hereby incorporated in its entirety including all tables, figures and claims.

SEQUENCE LISTING

The instant application contains a Sequence Listing which has been submitted in ASCII format via EFS-Web and is hereby incorporated by reference in its entirety. Said ASCII copy, created on Dec. 9, 2016, is named OHNO_003_US_SeqListing.txt and is 20 kilobytes in size

TECHNICAL FIELD

The present invention relates to a calcium indicator gene. More specifically, the present invention relates to a fluorescent protein that functions as a calcium sensor, which is a fluorescent calcium indicator protein having an excellent fluorescent characteristic and calcium reactivity.

BACKGROUND ART

Calcium plays an essential role in maintaining and regulating biological functions, as a regulatory factor for various cellular functions such as muscle contraction, neural excitability, hormonal secretion, and changes in enzyme activities. For measurement of in vivo (extracellular and intracellular) calcium concentrations, proteins referred to as calcium sensors (calcium indicators) have been conventionally used.

In recent years, for analyzing cognitive activities, which are the essence of higher functions of the brain, at the cellular level or intracellular domain level, a technique for ultra-fast imaging of changes in calcium concentration evoked by neural activities is required, and the development of a fluorescent calcium sensor having excellent calcium reactivity is desired.

As a protein that functions as a calcium sensor, a calcium indicator protein is known in which a partial sequence of calmodulin and a partial sequence of myosin light chain kinase are linked to a fluorescent protein. This calcium indicator protein utilizes the phenomenon in which binding of calcium to the partial sequence of calmodulin causes a change in the conformation of the protein, which causes a change in the intensity of fluorescence emitted by the fluorescent protein (GFP or RFP). Non Patent Literature 1, for example, describes a calcium indicator protein (R-GECO1) obtained using mApple as a fluorescent protein. Patent Literature 1 discloses R-CaMP1.01 prepared by modifying R-GECO1, which exhibits a change in fluorescence intensity greater than that of R-GECO1, and R-CaMP1.07 prepared by modifying R-CaMP1.01, which exhibits a change in fluorescence intensity even greater than that of R-CaMP1.01, and has been improved in terms of intracellular localization.

CITATION LIST

Patent Literature

Patent Literature 1: Japanese Patent Laid-Open No. 2014-1161

Non Patent Literature

Non Patent Literature 1: Science, 2011, 333, 1888-1891

SUMMARY OF INVENTION

Technical Problem

A principal object of the present invention is to provide a calcium indicator protein having a fluorescent characteristic and calcium reactivity superior to those of conventional calcium indicator proteins.

Solution to Problem

To solve the above-described problem, the present invention provides [1] to [23] set forth below.

[1] DNA in which one coding derivative of a nucleotide sequence encoding a calmodulin-binding sequence (hereinafter, "ckkap sequence") of calcium/calmodulin-dependent protein kinase kinase and a nucleotide sequence encoding a calcium-binding sequence (hereinafter, "CaM sequence") of calmodulin is linked to a 5' end of a nucleotide sequence encoding a fluorescent protein, and the other nucleotide sequence is linked to a 3' end of the nucleotide sequence encoding the fluorescent protein.

[2] The DNA according to [1], wherein one coding derivative of the nucleotide sequence encoding the ckkap sequence is linked to the 5' end of the nucleotide sequence encoding the fluorescent protein, and the nucleotide sequence encoding the CaM sequence is linked to the 3' end of the nucleotide sequence encoding the fluorescent protein.

[3] The DNA according to [1] or [2], wherein the coding derivative of the nucleotide sequence encoding the ckkap sequence is any one of the base sequences set forth in SEQ ID NOS: 1 to 3.

[4] The DNA according to any of [1] to [3], wherein the nucleotide sequence encoding one coding derivative of the ckkap sequence and the nucleotide sequence encoding the fluorescent protein, as well as the nucleotide sequence encoding the fluorescent protein and the nucleotide sequence encoding the CaM sequence, are each linked via a nucleotide sequence encoding an amino acid linker.

[5] The DNA according to [4], wherein the nucleotide sequence encoding one coding derivative of the ckkap sequence is linked to the 5' end of the nucleotide sequence encoding the fluorescent protein, and the nucleotide sequence encoding the CaM sequence is linked to the 3' end of the nucleotide sequence encoding the fluorescent protein, the nucleotide sequence encoding one coding derivative of the ckkap sequence and the nucleotide sequence encoding the fluorescent protein are linked via a nucleotide sequence encoding an amino acid linker A, and the nucleotide sequence encoding the fluorescent protein and the nucleotide sequence encoding the CaM sequence are linked via a nucleotide sequence encoding an amino acid linker B, and wherein a combination of the amino acid linker A and the amino acid linker B is any one of the following combinations:

the amino acid linker A (-Pro-Val-) and the amino acid linker B (-Thr-Arg);

the amino acid linker A (-Leu-Asp-) and the amino acid linker B (-Thr-Asp-);

the amino acid linker A (-Met-Asp-) and the amino acid linker B (-Thr-Asp-);

the amino acid linker A (-Leu-Glu-) and the amino acid linker B (-Thr-Asp-);

the amino acid linker A (-Arg-Asp-) and the amino acid linker B (-Thr-Lys-);

the amino acid linker A (-Arg-Asp-) and the amino acid linker B (-Phe-Pro-);

the amino acid linker A (-Phe-Asp-) and the amino acid linker B (-Ala-Asp-);

the amino acid linker A (-Phe-Asp-) and the amino acid linker B (-Thr-Asp-);

the amino acid linker A (-Gln-Asp-) and the amino acid linker B (-Thr-Asp-); and the amino acid linker A (-Phe-Asp-) and the amino acid linker B (-Phe-Asp-).

[6] The DNA according to any of [1] to [5], wherein the nucleotide sequence encoding the CaM sequence is the base sequence set forth in SEQ ID NO: 7 or 8.

[7] A vector comprising the DNA according to any of [1] to [6].

[8] A transformed cell transfected with a calcium indicator gene in which one coding derivative of a nucleotide sequence encoding a ckkap sequence and a nucleotide sequence encoding a CaM sequence is linked to a 5' end of a nucleotide sequence encoding a fluorescent protein, and the other nucleotide sequence is linked to a 3' end of the nucleotide sequence encoding the fluorescent protein.

[9] A transgenic animal, excluding a human, transfected with a calcium indicator gene in which one coding derivative of a nucleotide sequence encoding a ckkap sequence and a nucleotide sequence encoding a CaM sequence is linked to a 5' end of a nucleotide sequence encoding a fluorescent protein, and the other nucleotide sequence is linked to a 3' end of the nucleotide sequence encoding the fluorescent protein.

[10] The transgenic animal according to [8] or [9], wherein one coding derivative of the nucleotide sequence encoding the ckkap sequence is linked to the 5' end of the nucleotide sequence encoding the fluorescent protein, and the nucleotide sequence encoding the CaM sequence is linked to the 3' end of the nucleotide sequence encoding the fluorescent protein in the calcium indicator gene.

[11] The cell according to [8] or the transgenic animal according to [9], wherein one coding derivative of the nucleotide sequence encoding the ckkap sequence is any one of the base sequences set forth in SEQ ID NOS: 1 to 3.

[12] The cell according to [8] or the transgenic animal according to [9], wherein one coding derivative of the nucleotide sequence encoding the CaM sequence is the base sequence set forth in SEQ ID NO: 7 or 8.

[13] A protein in which one coding derivative of a ckkap sequence and a CaM sequence is linked to an N-terminus of a fluorescent protein, and the other is linked to a C-terminus of the fluorescent protein.

[14] The protein according to [13], wherein one coding derivative of the ckkap sequence is linked to the N-terminus of the fluorescent protein, and the CaM sequence is linked to the C-terminus of the fluorescent protein.

[15] The protein according to [13] or [14], wherein one coding derivative of the ckkap sequence is any one of the amino acid sequences set forth in SEQ ID NOS: 4 to 6 and 15 to 19.

[16] The protein according to any of [13] to [15], wherein the CaM sequence is the amino acid sequence set forth in SEQ ID NO: 9 or 10.

[17] The protein according to any of [13] to [16], wherein one coding derivative of the ckkap sequence and the fluorescent protein, as well as the fluorescent protein and the CaM sequence, are each linked via an amino acid linker.

[18] The protein according to [17], wherein the one coding derivative of ckkap sequence is linked to the N-terminus of the fluorescent protein, and the CaM sequence is linked to the C-terminus of the fluorescent protein, one coding derivative of the ckkap sequence and the fluorescent protein are linked via an amino acid linker A, and the fluorescent protein and the CaM sequence are linked via an amino acid linker B, and wherein a combination of the amino acid linker A and the amino acid linker B is any one of the following combinations:

the amino acid linker A (-Pro-Val-) and the amino acid linker B (-Thr-Arg);

the amino acid linker A (-Leu-Asp-) and the amino acid linker B (-Thr-Asp-);

the amino acid linker A (-Met-Asp-) and the amino acid linker B (-Thr-Asp-);

the amino acid linker A (-Leu-Glu-) and the amino acid linker B (-Thr-Asp-);

the amino acid linker A (-Arg-Asp-) and the amino acid linker B (-Thr-Lys-);

the amino acid linker A (-Arg-Asp-) and the amino acid linker B (-Phe-Pro-);

the amino acid linker A (-Phe-Asp-) and the amino acid linker B (-Ala-Asp-);

the amino acid linker A (-Phe-Asp-) and the amino acid linker B (-Thr-Asp-);

the amino acid linker A (-Gln-Asp-) and the amino acid linker B (-Thr-Asp-); and the amino acid linker A (-Phe-Asp-) and the amino acid linker B (-Phe-Asp-).

[19] A method of measuring an action potential in a cell comprising the step of detecting fluorescence emitted by a calcium indicator protein expressed in the cell, the calcium indicator protein being a calcium indicator protein in which one coding derivative of a ckkap sequence and a CaM sequence is linked to an N-terminus of a fluorescent protein, and the other is linked to a C-terminus of the fluorescent protein.

[20] A method of imaging a calcium ion in a cell comprising the step of detecting fluorescence emitted by a calcium indicator protein expressed in the cell, the calcium indicator protein being a calcium indicator protein in which one coding derivative of a ckkap sequence and a CaM sequence is linked to an N-terminus of an amino acid sequence of a fluorescent protein, and the other is linked to a C-terminus of the fluorescent protein.

[21] The method of measuring an action potential in a cell according to [19] or the method of imaging a calcium ion in a cell according to [20], comprising the step of transfecting the cell with a calcium indicator gene in which one coding derivative of a nucleotide sequence encoding a ckkap sequence and a nucleotide sequence encoding a CaM sequence is linked to a 5' end of a nucleotide sequence encoding a fluorescent protein, and the other nucleotide sequence is linked to a 3' end of the nucleotide sequence encoding the fluorescent protein.

[22] A calcium indicator reagent for measuring an action potential in a cell and/or imaging a calcium ion in a cell, the reagent comprising DNA in which one coding derivative of a nucleotide sequence encoding a ckkap sequence and a nucleotide sequence encoding a CaM sequence is linked to a 5' end of a nucleotide sequence encoding a fluorescent protein, and the other nucleotide sequence is linked to a 3' end of the nucleotide sequence encoding the fluorescent protein, or the reagent comprising a vector comprising the DNA.

[23] The reagent according to [22], wherein the cell is a neuron.

Advantageous Effects of Invention

In accordance with the present invention, there is provided a calcium indicator protein having an excellent fluorescent characteristic and calcium reactivity.

BRIEF DESCRIPTION OF DRAWINGS

FIG. 1 shows the structures of the calcium indicator protein R-CaMP2 according to the present invention and the calcium indicator protein R-CaMP1.07 according to a known technique.

FIG. 2A shows examples of amino acid sequences of coding derivatives of ckkap sequences of the calcium indicator protein according to the present invention.

FIG. 2B shows other examples of amino acid sequences of coding derivatives of ckkap sequences of the calcium indicator protein according to the present invention.

FIG. 3 shows $Ca^{2+}$ titration curves of R-CaMP1.07, R-CaMP2, and R-GECO2L; the curves were fit according to the Hill equation.

FIG. 15A shows single-trial responses of R-CaMP1.07 when clamped to five spikes and stimulated at difference frequencies in pyramidal cells in the layer ⅔ of the barrel field in acute slices.

FIG. 15B shows single-trial responses of R-CaMP2 when clamped to five spikes and stimulated at difference frequencies in pyramidal cells in the layer ⅔ of the barrel field in acute slices.

DESCRIPTION OF EMBODIMENTS

Figure 4:
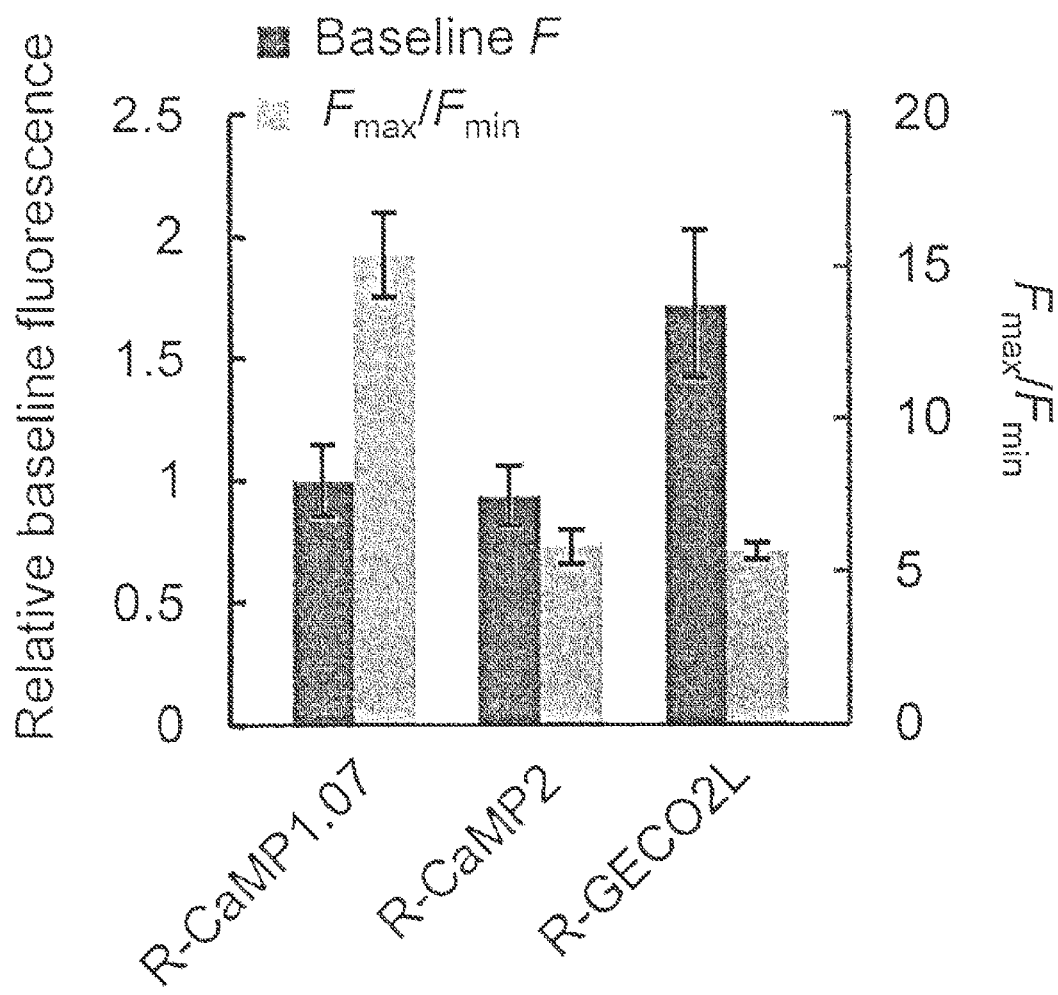
FIG. 4 shows baseline fluorescence intensities and dynamic ranges (Fmax/Fmin) in vitro of R-CaMP1.07, R-CaMP2, and R-GECO2L.

Preferred modes for carrying out the present invention will be described hereinafter, with reference to the drawings. Note that the embodiments described below merely illustrate representative embodiments of the present invention, which are not intended to narrow the interpretation of the scope of the present invention.

1. Calcium Indicator Gene and Calcium Indicator Protein

The calcium indicator gene and the calcium indicator protein according to the present invention will be described, taking the examples of "R-CaMP2" and "R-GECO2L", for example, described in the Examples.

The calcium indicator protein according to the present invention contains an amino acid sequence of a fluorescent protein, an amino acid sequence of a calmodulin-binding sequence (hereinafter, "ckkap sequence") of or derived from calcium/calmodulin-dependent protein kinase kinase (CaMKK), and an amino acid sequence of a calcium-binding sequence (hereinafter, "CaM sequence") of calmodulin. Similarly, the calcium indicator gene according to the present invention contains a nucleotide sequence encoding the fluorescent protein, a nucleotide sequence encoding the ckkap sequence, and a nucleotide sequence encoding the CaM sequence.

The calcium indicator protein according to the present invention may also have an amino acid linker that links one coding derivative of the ckkap sequence and the fluorescent protein, and an amino acid linker that links the fluorescent protein and the CaM sequence. Similarly, the calcium indicator gene according to the present invention may also have a nucleotide sequence encoding an amino acid linker that links one coding derivative of the ckkap sequence and the fluorescent protein, and a nucleotide sequence encoding an amino acid linker that links the fluorescent protein and the CaM sequence.

FIG. 1 shows one example of the structure of the calcium indicator protein (or the calcium indicator gene) according to the present invention. The upper section of the figure shows the structure of R-CaMP1.07, which is a conventional calcium indicator protein described in Patent Literature 1, and the lower section of the figure shows the structure of R-CaMP2, which is a calcium indicator protein according to the present invention. The designation "ckkap-WL" in the figure represents one preferable example of one coding derivative of the ckkap sequence. The designation "cpApple" represents a red fluorescent protein.

In R-CaMP2 according to the present invention, one coding derivative of the ckkap sequence is linked to the N-terminus, and the CaM sequence is linked to the C-terminus, of the amino acid sequence of the fluorescent protein, cpApple. Similarly, in the R-CaMP2 gene, a nucleotide sequence encoding one coding derivative of the ckkap sequence is linked to the 5' end, and a nucleotide sequence encoding the CaM sequence is linked to the 3' end, of a nucleotide sequence encoding the fluorescent protein, cpApple. This structure corresponds to a structure obtained by substituting the calmodulin-binding sequence of myosin light chain kinase designated by "M13" with one coding derivative of the ckkap sequence in conventional R-CaMP1.07. Moreover, R-GECO2L according to the present invention has a structure in which the M13 sequence of R-GECO1, which is a conventional calcium indicator protein described in Non Patent Literature 1, has been substituted with one coding derivative of the ckkap sequence. The full-length amino acid sequences of R-CaMP2 and R-GECO2L are shown in SEQ ID NO: 11 and SEQ ID NO: 13, respectively, and the full-length base sequences of the nucleotide sequences encoding R-CaMP2 and R-GECO2L are shown in SEQ ID NO: 12 and SEQ ID NO: 14, respectively.

R-CaMP2 according to the present invention may have an additional sequence at each of its N-terminus and C-terminus, as in R-CaMP1.07 described in Patent Literature 1. In the figure, the additional sequence (37 amino acid residues) designated by "MGS" is a tag sequence used in purifying the protein. The additional sequence (21 amino acid residues) designated by "F2A" functions to localize the protein in the cytoplasm within a cell.

The calcium indicator protein according to the present invention undergoes a change in conformation when calcium is bound to the CaM sequence, and one coding derivative of the ckkap sequence is bound to the calcium-binding CaM sequence. The calcium indicator protein according to the present invention undergoes a change in conformation in the presence of calcium to thereby cause a change in the conformation of the fluorescent protein and hence, a change in the fluorescent characteristic. In this way, the calcium indicator protein according to the present invention functions as a calcium sensor. As described in the Examples, R-CaMP2 and R-GECO2L, for example, according to the present invention, which have one coding derivative of the ckkap sequence as a binding domain for the calcium-binding CaM sequence, exhibits a fluorescent characteristic and calcium reactivity superior to those of conventional calcium indicator proteins such as R-CaMP1.07 and R-GECO1, which have the M13 sequence as the binding domain. More specifically, R-CaMP2 and R-GECO2L, for example, have characteristics superior to those of the conventional calcium indicator proteins, in that they exhibit a greater variation (dynamic range) between fluorescence intensities in the presence and absence of calcium, and exhibit a greater rate of change of the fluorescent characteristic caused by binding and dissociation of calcium.

The amino acid sequence of R-CaMP2 is shown in SEQ ID NO: 11. In the amino acid sequence shown in SEQ ID NO: 11, positions 1 to 37 correspond to the MGS sequence, positions 38 to 63 correspond to one coding derivative of the ckkap sequence (ckkap-WL), positions 66 to 307 correspond to the cpApple sequence, positions 310 to 456 correspond to the CaM sequence, and positions 472 to 492 correspond to the F2A sequence. Each of the MGS sequence, coding derivative of ckkap sequence, cpApple sequence, CaM sequence, and F2A sequence may be linked to an adjacent sequence via a linker. The linker is not particularly limited as long as the functions of the calcium indicator protein are maintained.

A preferable linker structure of R-CaMP2 is such that the amino acid linker A that links the one coding derivative of ckkap sequence and the fluorescent protein is "-Pro-Val-", and the amino acid linker B that links the fluorescent protein and the CaM sequence is "-Thr-Arg".

Examples of preferable combinations of the amino acid linkers A and B in the calcium indicator protein according to the present invention include, in addition to the above-described combination of "-Pro-Val-" and "-Thr-Arg", the following combinations:
the amino acid linker A (-Leu-Asp-) and the amino acid linker B (-Thr-Asp-);
the amino acid linker A (-Met-Asp-) and the amino acid linker B (-Thr-Asp-);
the amino acid linker A (-Leu-Glu-) and the amino acid linker B (-Thr-Asp-);
the amino acid linker A (-Arg-Asp-) and the amino acid linker B (-Thr-Lys-);
the amino acid linker A (-Arg-Asp-) and the amino acid linker B (-Phe-Pro-);
the amino acid linker A (-Phe-Asp-) and the amino acid linker B (-Ala-Asp-);
the amino acid linker A (-Phe-Asp-) and the amino acid linker B (-Thr-Asp-);
the amino acid linker A (-Gln-Asp-) and the amino acid linker B (-Thr-Asp-); and
the amino acid linker A (-Phe-Asp-) and the amino acid linker B (-Phe-Asp-).

By adopting these linker structures, a calcium indicator protein having high fluorescence intensity in the presence of calcium and having a large dynamic range can be achieved.

The amino acid sequence of R-GECO2L is also shown in SEQ ID NO: 13. In the amino acid sequence shown in SEQ ID NO: 13, positions 1 to 3 correspond to the MGS sequence, positions 4 to 29 correspond to one coding derivative of the ckkap sequence (ckkap-WL), positions 32 to 273 correspond to the cpApple sequence, and positions 276 to 422 correspond to the CaM sequence. Each of the MGS sequence, coding derivative of ckkap sequence, cpApple sequence, and CaM sequence may be linked to an adjacent sequence via a linker.

[Ckkap Sequence]

The ckkap sequence of the calcium indicator protein according to the present invention is the calmodulin-binding sequence of calcium/calmodulin-dependent protein kinase kinase (CaMKK). While there are an α subunit and β subunit for the calmodulin-binding sequence of CaMKK, the coding derivatives of ckkap sequence of the present invention may either be an α subunit-derived sequence (the amino acid sequence is shown in SEQ ID NO: 4, and the nucleotide sequence encoding this amino acid sequence is shown in SEQ ID NO: 1) or a β subunit-derived sequence (the amino acid sequence is shown in SEQ ID NO: 5, and the nucleotide sequence encoding this amino acid sequence is shown in SEQ ID NO: 2). Note that although these sequences are derived from rat CaMKK, the coding derivatives of ckkap sequence may be from any biological species as long as it has the property of binding to the calcium-bound CaM sequence.

The coding derivatives of ckkap sequence may also be an amino acid sequence in which one or more (preferably 1 to 5) amino acids in the amino acid sequence shown in SEQ ID NO: 4 or 5 have been deleted, substituted, inserted, or added, as long as it has the property of binding to the calcium-bound CaM sequence. One example of such a coding derivative of ckkap sequence is ckkap-WL described above (the amino acid sequence is shown in SEQ ID NO: 6, and the nucleotide sequence encoding this amino acid sequence is shown in SEQ ID NO: 3). Amino acid sequences obtained by further modifying the amino acid sequence of ckkap-WL (ckkap-WL 2-6) can also be adopted as coding derivatives of the ckkap sequence. In view of enhancing the fluorescent characteristic and calcium reactivity of the calcium indicator protein, the amino acid sequence of the coding derivatives of ckkap sequence is preferably the amino acid sequence shown in any of SEQ ID NOS: 6 and 15 to 19, and most preferably the amino acid sequence shown in any of SEQ ID NOS: 15 to 19. The fluorescent characteristic or calcium reactivity of the calcium indicator protein can also be adjusted to a desired degree, by appropriately selecting the amino acid sequence of the ckkap sequence from the sequences shown in SEQ ID NOS: 6 and 15 to 19. R-CaMP2 and R-GECO2L described in the Examples each contain ckkap-WL as the coding derivative of ckkap sequence. R-CaMP2_LLA contains ckkap-WL5 as the coding derivative of ckkap sequence. FIG. 2A shows the amino acid sequences of the α subunit-derived ckkap sequence (ckkap α) and β subunit-derived ckkap sequence (ckkap β), as well as the amino acid sequence of ckkap-WL. FIG. 2B shows the amino acid sequences of ckkap-WL2 to 6.

Note that the coding derivatives of ckkap sequence is not limited to those consisting only of the calmodulin-binding sequence of CaMKK. Specifically, the ckkap sequence may contain an amino acid sequence of the amino acid sequence of CaMKK other than the calmodulin-binding sequence, and may contain, for example, several to several tens of amino acid residues at the N-terminus and/or C-terminus of the calmodulin-binding sequence.

[CaM Sequence]

The CaM sequence of the calcium indicator protein according to the present invention is the calcium-binding sequence of calmodulin. The amino acid sequence shown in SEQ ID NO: 9 or SEQ ID NO: 10 can be used as the CaM sequence. The amino acid sequence shown in SEQ ID NO: 9 is the CaM sequence included in R-CaMP2, and the amino acid sequence shown in SEQ ID NO: 10 is the CaM sequence included in R-GECO2L. Each of these CaM sequences, which is derived from an amino acid sequence of rat calmodulin from positions 2 to 148, is an amino acid sequence obtained by introducing a substitution of 4 or 5 amino acid residues into the amino acid sequence. The base sequence of a nucleotide sequence encoding the CaM sequence of R-CaMP2 is shown in SEQ ID NO: 7, and the base sequence of a nucleotide sequence encoding the CaM sequence of R-GECO2L is shown in SEQ ID NO: 8. Note that the CaM sequence may be derived from any biological species as long as it has the property of binding to calcium, and can bind to the ckkap sequence with calcium being bound thereto.

The CaM sequence may also be an amino acid sequence in which one or more (preferably 1 to 5) amino acids in the amino acid sequence shown in SEQ ID NO: 9 or 10 have been deleted, substituted, inserted, or added, as long as it has the property of binding to calcium, and can bind to the ckkap sequence with calcium being bound thereto. Note that the CaM sequence is not limited to those consisting only of the calcium-binding sequence of calmodulin. Specifically, the CaM sequence may contain an amino acid sequence of the calcium-binding sequence of calmodulin other than the calcium-binding sequence, and may contain, for example, several to several tens of amino acid residues at the N-terminus and/or C-terminus of the calcium-binding sequence.

[Fluorescent Protein]

Examples of fluorescent proteins used as the fluorescent protein of the calcium indicator protein according to the present invention include, but are not particularly limited to, a blue fluorescent protein (for example, BFP in X-CaMP-Blue described in the Examples), a green fluorescent protein (for example, EGFP in X-CaMPGreen described in the Examples), a yellow fluorescent protein (for example, Venus in X-CaMPYellow described in the Examples), and a red fluorescent protein. In particular, a red fluorescent protein is preferably used, and mApple or a modified product thereof, for example, may be used. Where the calcium indicator protein is used for manipulating cellular functions by photostimulation, and simultaneously measuring the cellular functions by fluorescent calcium imaging, the fluorescent protein is preferably a red fluorescent protein, because its excitation wavelength does not overlap with that of a photostimulation probe, Channelrhodopsin-2, which is generally used for the purpose of cellular function manipulation.

The modified product of mApple is a product obtained by modifying the structure of the protein by cleaving the amino acid sequence of mApple near an amino acid residue that affects the fluorescent characteristic, and by substituting an amino acid residue at a specific site. Specific examples of the modified product of mApple are described in Patent Literature 1.

FIG. 1 illustrates an example of the calcium indicator protein (or calcium indicator gene) according to the present invention in which one coding derivative of the ckkap sequence, the fluorescent protein, and the CaM sequence are aligned in this order from the N-terminus (or the 5' end) to the C-terminus (or the 3' end). In the calcium indicator protein according to the present invention, this order of alignment, i.e., one coding derivative of the ckkap sequence, the fluorescent protein, and the CaM sequence, may be replaced by the CaM sequence, the fluorescent protein, and one coding derivative of the ckkap sequence, from the N-terminus to the C-terminus.

The calcium indicator protein according to the present invention undergoes a change in conformation upon binding with calcium, which affects the conformation of the fluorescent protein included in the calcium indicator protein, thereby causing the fluorescent characteristic of the fluorescent protein to reversibly change. As used herein, the "fluorescent characteristic" refers to a fluorescent characteristic such as fluorescence intensity, fluorescence wavelength, fluorescence intensity ratio, absorbance, or absorption wavelength. Fluorescence intensity is used in the present invention as one example of the fluorescent characteristic. When the change in the fluorescent characteristic represents a change in fluorescence intensity, a variation in fluorescence, $\Delta F/F$, is preferably at least 0.3, and more preferably 0.6 or more.

The calcium indicator protein according to the present invention includes one coding derivative of the ckkap sequence so that, upon binding with calcium, it causes a greater change in the fluorescent characteristic than that in a conventional calcium indicator protein. As used herein, the "greater change in the fluorescent characteristic" means that when the change in the fluorescent characteristic represents a change in fluorescence intensity, the variation in fluorescence, $\Delta F/F$, is greater than that in a conventional calcium sensor, and is preferably augmented 3-fold or more.

2. Vector, Transformed Cell, and Transgenic Animal

The calcium indicator gene according to the present invention can be prepared using a known genetic engineering technique. The calcium indicator gene according to the present invention can be prepared by, for example, amplifying each of the nucleotide sequences encoding one coding derivative of the ckkap sequence, the fluorescent protein, and the CaM sequence by PCR, and connecting the amplified fragments.

The obtained calcium indicator gene can be incorporated into a known vector such as a plasmid or a virus. A transformed cell expressing the calcium indicator protein can be obtained by transfecting the vector carrying the calcium indicator gene into a desired cell. The vector carrying the calcium indicator gene or the calcium indicator gene per se can form a part of the below-described reagent for measuring an action potential in a cell or imaging a calcium ion in a cell.

Moreover, a transgenic animal transfected with the calcium indicator gene can be prepared using a known genetic engineering technique. Such a transgenic animal can be prepared by transfecting the calcium indicator gene into a totipotent cell of a mammal to develop this cell into individuals, and selecting for an individual transfected with the calcium indicator gene in the genome of somatic cells. In this case, the calcium indicator gene may be transfected and incorporated under the control of a tissue-specific promoter to thereby obtain a transgenic animal expressing the calcium indicator protein only in brain neurons, for example.

3. The Method of Measuring an Action Potential in a Cell and the Method of Imaging a Calcium Ion in a Cell The calcium indicator protein according to the present invention can detect a change in intracellular calcium concentration with high sensitivity, and thus, can be suitably used for measuring an action potential in a cell and imaging calcium in a cell. One preferable example of the cell is a neuron, although not particularly limited thereto.

For example, a vector carrying the calcium indicator gene according to the preset invention is transfected into a cell to be measured for expression of the calcium indicator protein. Alternatively, a transgenic animal expressing the calcium indicator protein in the cell to be measured is prepared. Then, the cell to be measured is irradiated, using a fluorescence microscope, a multiphoton microscope, or the like, with excitation light at a wavelength corresponding to the excitation wavelength of the fluorescent protein included in the calcium indicator protein, and fluorescence emitted by the calcium indicator protein is detected. Action potentials of the cell can be measured by acquiring changes in fluorescence intensity with time, or intracellular calcium can be imaged by performing real-time image processing of changes in fluorescence intensity.

The method of measuring an action potential in a cell and the method of imaging a calcium ion in a cell, which use the calcium indicator protein according to the present invention, can be applied to the screening for substances that affect the cellular action potential and the intracellular calcium ion concentration. For example, animals to which test substances have been administered or cells treated with the test substances at the individual level, tissue level, or cellular level are used, and cellular action potentials or the like in cells are recorded. The recorded cellular action potentials are then compared with cellular action potentials or the like acquired in the same manner without treatment with the test substances. Then, it is determined whether or not the test substances affect the cellular action potentials or the like. Then, substances that function to increase or suppress the cellular action potentials or the like are selected. The test substances may be various synthetic or natural compounds, peptides, proteins, and nucleic acids such as DNA and RNA, for example. When a nucleic acid is used, the gene encoded by the nucleic acid is expressed in cells by transfection, and then the change of the cellular action potentials or the like are recorded.

Examples

1. Materials and methods

[R-CaMP2 and R-GECO2L]

An R-CaMP1.07 expression construct was constructed in accordance with the technique described in the document (PLoS One, 2012, 7, e39933). R-GECO1 was obtained from Addgene. R-GECO1 was subcloned into a pCMV vector derived from pEGFP-N1 (Clontech).

The M13 sequence of R-CaMP1.07 and R-GECO1 was substituted with one coding derivative of a $Ca^{2+}$/calmodulin-binding sequence (ckkap sequence) corresponding to Val438-Phe463 of rat CaMKK α to prepare R-CaMP2 and R-GECO2L (see FIG. 1). One coding derivative consisting of a hybrid sequence (ckkap-WL, SEQ ID NO: 6) of the sequence of CaMKK α (ckkap α, SEQ ID NO: 4) and the sequence of CaMKK β (ckkap β, SEQ ID NO: 5) was prepared by site-directed mutagenesis, and used as the ckkap sequence (see FIG. 2A). The amino acid substitutions described in the document (Nature, 2013, 499, 295-300, J. Biol. Chem., 2009, 284, 6455-6464) were introduced into the CaM sequences (SEQ ID NOS: 8 and 9). R-CaMP2 and R-GECO2L were subcloned into the pCAG vector.

[R-CaMP2_LLA]

One coding derivative of the ckkap sequence (ckkap-WL) of R-CaMP2 was modified by site-directed mutagenesis to prepare R-CaMP2_LLA containing ckkap-WL5 as the ckkap sequence (see FIG. 2B).

[X-CaMPBlue, X-CaMPGreen, and X-CaMPYellow]

The M13 sequence of G-CaMP4.1 described in the document (PLos One, 2010, Vol. 5, No. 2, e8897) was substituted with one coding derivative of the ckkap sequence (ckkap- WL). Then, BFP, EGFP, or Venus was incorporated as the fluorescent protein into the resulting product to obtain X-CaMPBlue, X-CaMPGreen, or X-CaMPYellow, respectively.

The following combinations of the amino acid linker A linking one coding derivative of the ckkap sequence and the fluorescent protein and the amino acid linker B linking the fluorescent protein and the CaM sequence were adopted.

X-CaMPBlue:
the amino acid linker A (-Leu-Asp-) and the amino acid linker B (-Thr-Asp-); or
the amino acid linker A (-Met-Asp-) and the amino acid linker B (-Thr-Asp-).

X-CaMPGreen:
the amino acid linker A (-Leu-Glu-) and the amino acid linker B (-Thr-Asp-);
the amino acid linker A (-Arg-Asp-) and the amino acid linker B (-Thr-Lys-); or
the amino acid linker A (-Arg-Asp-) and the amino acid linker B (-Phe-Pro-).

X-CaMPYellow:
the amino acid linker A (-Phe-Asp-) and the amino acid linker B (-Ala-Asp-);
the amino acid linker A (-Phe-Asp-) and the amino acid linker B (-Thr-Asp-);
the amino acid linker A (-Gln-Asp-) and the amino acid linker B (-Thr-Asp-); or
the amino acid linker A (-Phe-Asp-) and the amino acid linker B (-Phe-Asp-).

[In Vitro $Ca^{2+}$ Fluorescence Measurement]

Each of the prepared calcium indicator proteins was expressed in HEK293T cells, and the cells were collected in a $Ca^{2+}$-free buffer (20 mM MOPS (pH 7.5), 100 mM potassium chloride, 1 mM DTT, 1× Protease Inhibitor Cocktail (Complete, EDTA Free, Roche)). After collected, the cells were subjected to ultrasonic disruption, centrifugation, and supernatant removal to obtain a lysate. This lysate was used for screening or the evaluation of in vitro performance.

In vitro fluorescence measurement was performed at room temperature, using a plate reader (Fusion a; Perkin Elmer) and 96-well plates. The dynamic range was calculated as Fmax/Fmin. Fmax was obtained by measuring the fluorescence intensity when $Ca^{2+}$ reached saturation at 0.3 mM $Ca^{2+}$, and Fmin was obtained by measuring the fluorescence intensity at zero $Ca^{2+}$ in the presence of 15 mM EGTA. $Ca^{2+}$ titration curves were calibrated with a mixed solution of 10 mM $K_2H_2EGTA$ and $Ca_2EGTA$, using a commercial kit ($Ca^{2+}$ Calibration Kit #1; Invitrogen). The Kd value and Hill coefficient were calculated by curve fitting, using analysis software (Origin Pro 7.5, Origin Lab).

[$Ca^{2+}$ Imaging in Cultured Hippocampal Neurons]

Dissociated hippocampal culture was performed in accordance with the technique described in the document (Cell, 1996, 87, 1203-1214, Cell Rep., 2013, 3, 978-987). The cultured hippocampal neurons were extracted from the hippocampus (CA1/CA3 region) of SD rats (Japan SLC) at the day of birth. At days 10 to 11 after the culture, the gene encoding the calcium indicator protein under the CMV promoter was transfected into the neurons by lipofection. At 2 or 3 days after the transfection, electrical field stimulation-evoked $Ca^{2+}$ imaging was performed using Tyrode solution (129 mM NaCl, 5 mM KCl, 30 mM glucose, 25 mM HEPES-NaOH [pH 7.4], 1 mM $MgCl_2$ and 3 mM $CaCl_2$). To prevent spontaneous firing, 10 µM CNQX (Tocris Bioscience) and 50 µM D-AP5 (Tocris Bioscience) were added to the Tyrode solution.

Synaptic boutons (sites at least 100 µm away from the axon initial segment, and showing an at least 3-fold increase in axon diameter) were imaged using an inverted microscope (IX81; Olympus) and an EM-CCD (C9100-12 or C9100-13; Hamamatsu Photonics). The neurons were maintained at 37° C. in a stage $CO_2$ incubator. The neurons were stimulated using an electrical field stimulation (50 mA, 1 msec current pulses). These stimulation conditions were sufficient to reliably evoke somatic spikes, using a pulse stimulator (Master-8; A.M.P.I.).

For UV-uncaging of glutamate, the neurons were imaged in $Mg^{2+}$-free Tyrode solution treated with 0.4 mM MNI-glutamate (Tocris Bioscience) and 1 µM TTX. UV-uncaging of MNI-glutamate was evoked using an ultraviolet photolysis system (Hamamatsu Photonics) operating on an AQUA-COSMOS software platform (Hamamatsu Photonics) and a UV nanosecond pulsed laser (Polaris II, New Wave Research) at 355 nm controlled with the system (Cell Rep., 2013, 3, 978-987).

[Intrauterine Electroporation]

Intrauterine electroporation was performed in accordance with the method described in the document (J. Neurosci., 2009, 29, 13720-13729). About 1.0 µl of a purified plasmid solution was injected into the lateral ventricle of anesthetized ICR mice (SLC Japan) at embryonic day 14.5, and five electrical pulses (45 V, 1 Hz, a duration of 50 msec, five times) were delivered by an electroporator (BTX). To visualize the mice or cells expressing the calcium indicator protein, EGFP was co-expressed as a volume control. Mice at postnatal weeks 4 to 7 were subjected to acute slice preparation or in vivo imaging.

[Simultaneous $Ca^{2+}$ Imaging and Whole-Cell Recording in Acute Brain Slices]

Acute brain slice experiments were performed in accordance with the technique described in the document (Eur. J. Neurosci., 2014, 39, 1720-1728). The 4- to 7-week-old mice were deeply anesthetized by $CO_2$ and decapitated. The calcium indicator protein was expressed under a CAG promoter, or with a tetracycline-inducible expression system using a TRE-tight promoter and Tet3G (Clontech and Tet-Systems).

Whole brains were quickly removed and immersed in ice-cold artificial cerebrospinal fluid (ACSF) (125 mM NaCl, 2.5 mM KCl, 1.25 mM $NaH_2PO_4$, 26 mM $NaHCO_3$, 2 mM $CaCl_2$, 1 mM $MgCl_2$, 25 mM glucose, bubbled with 95% $O_2$ and 5% $CO_2$). Acute coronal brain slices of the somatosensory area (thickness: 250 µm) were cut using a microtome (VT1200S, Leica). The brain slices were cultured for 30 minutes in oxygenated ACSF at 30° C. and then maintained at room temperature before being transferred to the recording chamber.

The brain slices were mounted on the immersion-type recording chamber on a two-photon microscope stage, and the layer 4 of the barrel field was identified by bright-field imaging. Whole-cell patch-clamp recording was performed in the layer ⅔ pyramidal cells of the barrel field. During the recording, the recording chamber was continuously perfused with oxygenated ACSF at 30° C. Patch pipettes were pulled from borosilicate glass capillaries using a vertical puller (PC-10; Narishige) and had a resistance of 5 to 8 M ohm when filled with the intracellular solution (133 mM K-$MeSO_3$, 7.4 mM KCl, 10 mM HEPES, 3 mM $Na_2ATP$, 0.3 mM $Na_2GTP$, 0.3 mM $MgCl_2$). Whole-cell current-clamp recording was performed using an EPC10 amplifier (Heka). All electrophysiological data were filtered at 10 kHz and digitized at 20 kHz.

[Cranial Surgery for In Vivo Imaging]

For in vivo imaging, mice (4-7 weeks old) were anesthetized by intraperitoneal administration of urethane (1.5 to 1.8 mg/g). The body temperature was maintained at 37° C. with a heating pad (FHC, Bowdoin). A stainless steel head plate was glued to the skull, using superglue and dental cement, above the right barrel field (3.0 to 3.5 mm lateral and 1.5 mm posterior to the bregma). A circular craniotomy (1.8 to 2.0 mm in diameter) was made, and the dura mater was carefully removed. The craniotomy was filled with a solution (150 mM NaCl, 2.5 mM KCl, 10 mM HEPES, 2 mM $CaCl_2$, 1 mM $MgCl_2$, 1.5% agarose, pH 7.3). To suppress the motion of the exposed brain, a glass coverslip was placed over the agarose. The mice were then transferred to the animal stage under the two-photon microscope.

[In Vivo Two-Photon $Ca^{2+}$ Imaging]

In vivo $Ca^{2+}$ imaging of calcium indicator protein-expressing neurons was performed in the layer ⅔ of the right barrel field (about 150 to 300 µm below the pia mater). Expression of the calcium indicator protein was driven by a CAG promoter. CAG promoter-driven persistent expression of the calcium indicator protein did not result in measurable neuronal toxicity.

Sensory stimulation was applied to contralateral whiskers by using a brief air puff (40 to 45 psi, 50 msec). Spontaneous and sensory-evoked activities of neuronal populations were acquired at a resolution of 256×192 pixels (sampling rate=2.3 Hz) for 3 minutes. For fast imaging of $Ca^{2+}$ transients in single neurons, high-speed line scan (sampling rate=650 to 700 Hz) was performed at the soma of the cortical neurons. For dendritic imaging, a focal plane with as many visible spines and dendrites as possible was chosen. Imaging was acquired at a resolution of 232×64 pixels (sampling rate=4.3 Hz) for 22 seconds.

[Simultaneous $Ca^{2+}$ Imaging and In Vivo Loose-Seal Cell Attached Electrical Recording]

In vivo cell-attached recording was performed using a glass electrode (5 to 7 M ohm) filled with ACSF containing a fluorescent substance (Alexa 488, 50 µM). The two-photon targeted patching method (Neuron, 2003, 39, 911-918) was applied to the calcium indicator protein-expressing neurons in the barrel field. About 10 minutes after the establishment of cell attachment, simultaneous measurements of spike recording and fast line-scan $Ca^{2+}$ imaging (sampling rate=675 Hz) were performed at the soma. Electrophysiological data were amplified using an EPC10 amplifier (Heka) in clamp mode. The electrophysiological data were filtered at 10 kHz and digitized at 20 kHz. Further, the electrophysiological data were high-pass filtered at 100 Hz off-line. The spikes were detected and counted automatically by thresholding using MATLAB.

For the materials and methods described above, reference may be made to the document (Nature Method, 2015, Vol. 12, No. 1, p. 64-70) published after the priority date of the present application.

2. Results

R-CaMP2 and R-GECO2L had Kd values of 100 nM or less (see FIG. 3). Moreover, R-CaMP2 and R-GECO2L showed baseline fluorescence values in the absence of $Ca^{2+}$ equivalent to or not more than 2-fold higher than that of R-CaMP1.07, and showed dynamic ranges of not less than 5-fold, although inferior to R-CaMP1.07 (see FIG. 4).

Figure 5A:
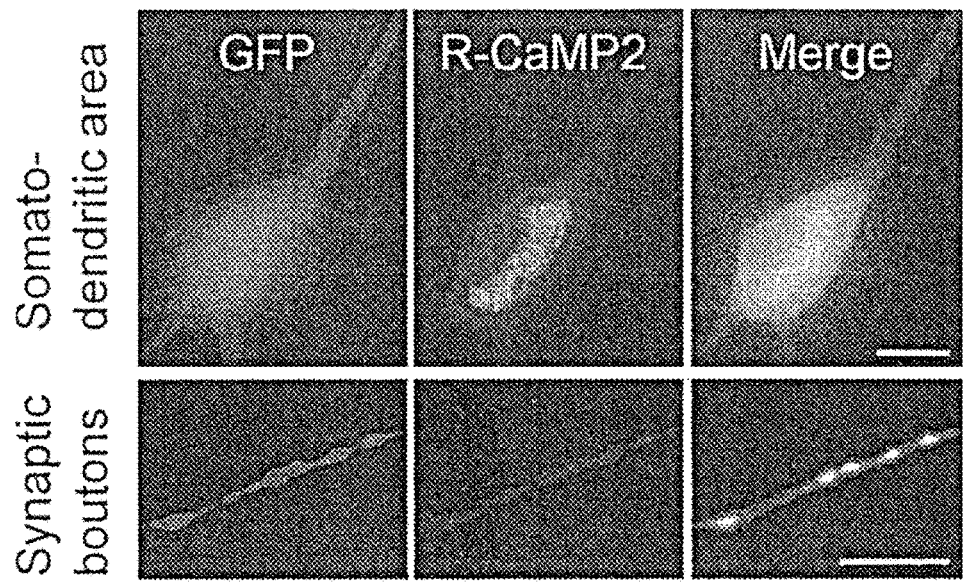
FIG. 5A shows cultured hippocampal neurons expressing EGFP and R-CaMP2.
Figure 5B:
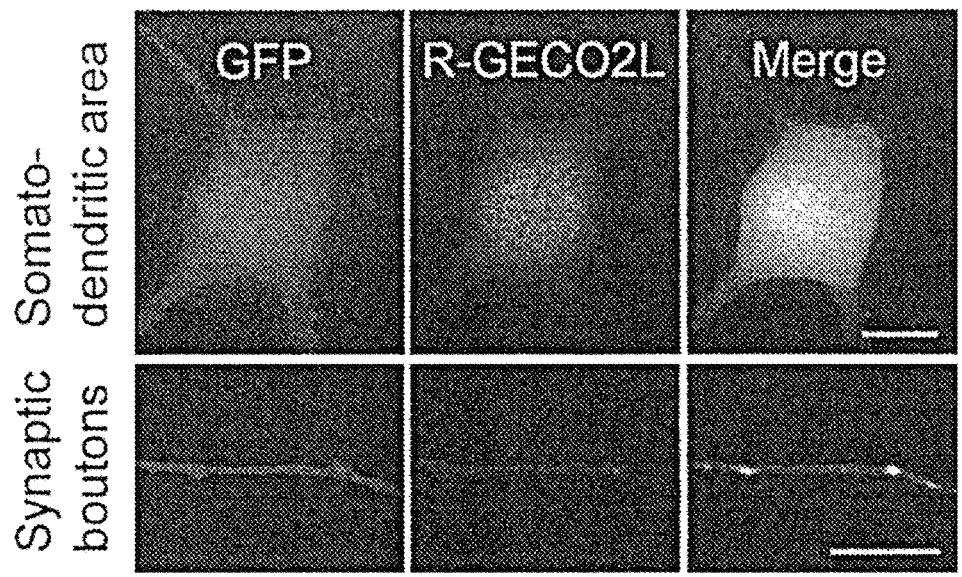
FIG. 5B shows cultured hippocampal neurons expressing EGFP and R-GECO2L. Scale bars: 10 μm.

R-CaMP2 and R-GECO2L were expressed in primary cultured hippocampal neurons. EGFP, of which fluorescence spectrum is separated from that of the red indicator, was expressed as a volume control. R-CaMP2 showed characteristic extranuclear localization (FIG. 5A). R-GECO2L, on the other hand, showed localization not only into the cytoplasm but also into the nucleus (FIG. 5B). Moreover, R-CaMP2 and R-GECO2L showed uniform distributions in dendrites, axons, and synaptic boutons.

Figure 6:
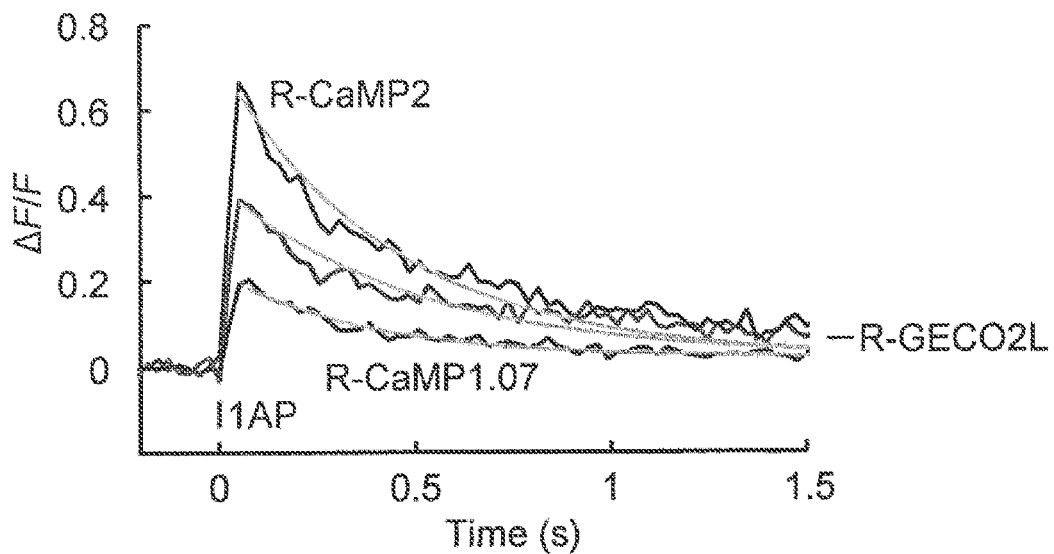
FIG. 6 shows fluorescence changes in response to field stimulation-evoked single action potentials, recorded from synaptic boutons of cultured hippocampal neurons.
Figure 7:
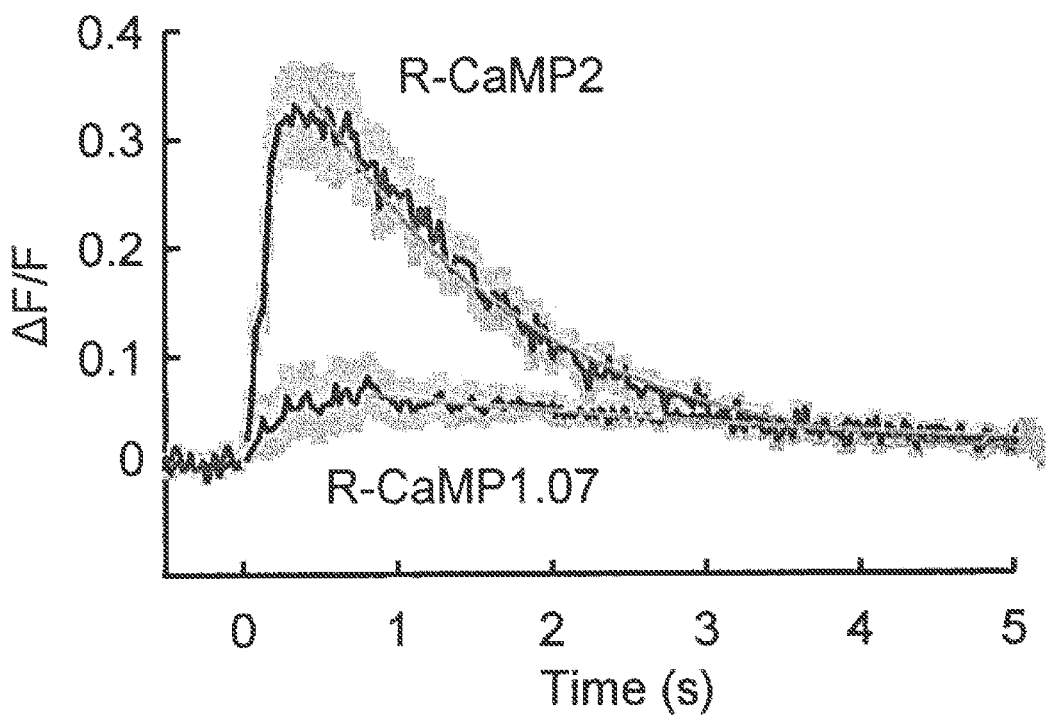
FIG. 7 shows fluorescence changes in response to a single UV-uncaging pulse of MNI-glutamate, recorded from the soma of cultured hippocampal neurons.

Electrical field stimulation-evoked single action potentials (1APs) (FIG. 6) and uncaging of MNI-glutamate near the soma by a single nanosecond pulse using a UV pulse laser (FIG. 7) generated significant $Ca^{2+}$ transients, which could be fitted with single exponential functions.

Figure 8:
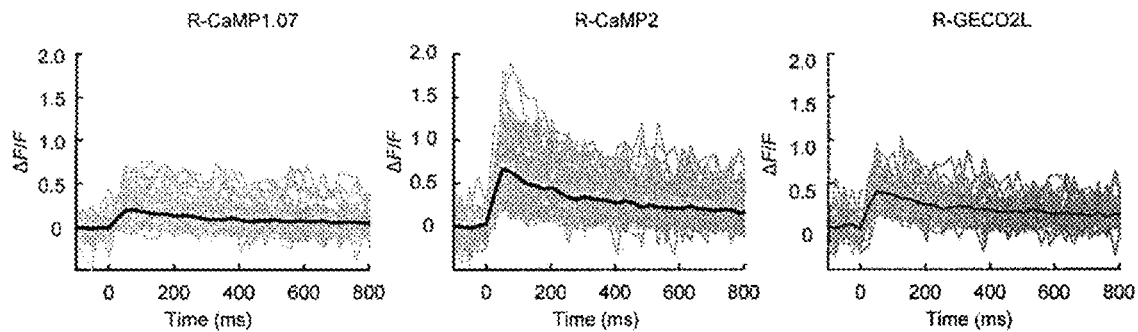
FIG. 8 shows traces of one trial (gray) and an average response of individual trials of each of R-CaMP1.07, R-CaMP2, and R-GECO2L in single action potential-evoked $Ca^{2+}$ imaging in synaptic boutons.
Figure 9:
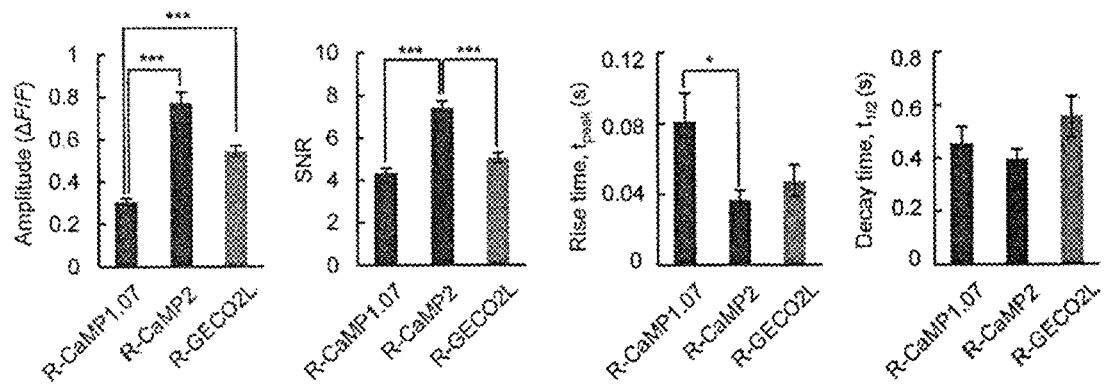
FIG. 9 shows single action potential amplitudes, SNRs, rise times, and decay time constants in single action potential-evoked $Ca^{2+}$ imaging in synaptic boutons.
Figure 10:
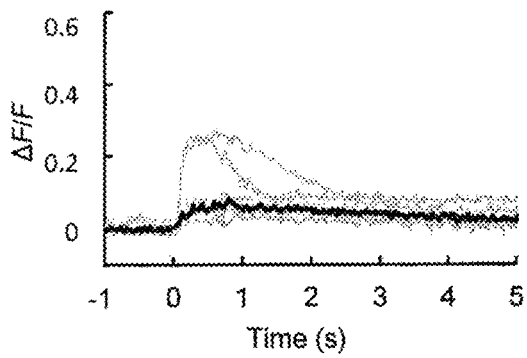
FIG. 10A shows traces of a single trial (n=9) and an average response of individual trials in response to a single pulse of glutamate uncaging in the soma of cultured hippocampal neurons expressing R-CaMP1.07.
FIG. 10B shows traces of a single trial (n=9) and an average response of individual trials in response to a single pulse of glutamate uncaging in the soma of cultured hippocampal neurons expressing R-CaMP2.
Figure 10:
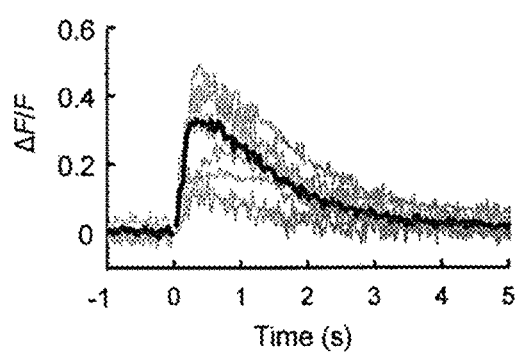
Figure 11:
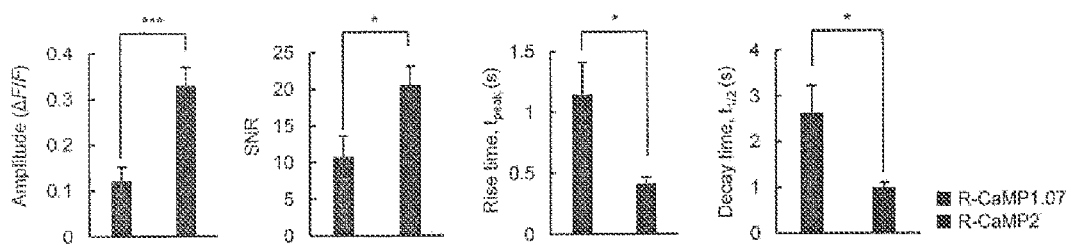
FIG. 11 shows amplitudes, SNRs, rise times, and decay time constants in response to a single pulse of glutamate uncaging in the soma of cultured hippocampal neurons.

R-CaMP2 and R-GECO2L showed much higher affinity for $Ca^{2+}$ than existing fluorescence calcium indicator proteins in vitro (Table 1). Additionally, R-CaMP2 and R-GECO2L had kinetics in living neurons faster than those of R-GECO1 and R-CaMP1.07 (FIGS. 8 to 11). Moreover, R-CaMP2 had a ΔF/F amplitude response not less than 3-fold larger than that of R-CaMP1.07, and larger than that of R-GECO2L (FIGS. 8 and 9).

TABLE 1

|  | dynamic range $F_{max}/F_{min}$ | Kd (nM) | Hill coefficient |
|---|---|---|---|
| R-GECO1 | 9.7 ± 0.7 | 223 ± 95 | 2.0 ± 0.2 |
| R-CaMP1.07 | 15.4 ± 1.4 | 192 ± 4 | 1.7 ± 0.1 |
| R-CaMP2 | 5.8 ± 0.6 | 69 ± 8 | 1.2 ± 0.1 |
| R-GECO2L | 5.1 ± 0.3 | 26 ± 3 | 1.3 ± 0.3 |
| GCaMP3 | 9.4 ± 0.2 | 365 ± 8 | 2.6 ± 0.1 |
| GCaMP5G | 19.2 ± 1.0 | 371 ± 13 | 2.8 ± 0.2 |
| GCaMP6f | 23.1 ± 3.0 | 296 ± 8 | 2.1 ± 0.1 |
| GCaMP6s | 31.8 ± 3.0 | 152 ± 8 | 2.7 ± 0.4 |
| G-CaMP6·X· | 11.4 ± 0.1 | 158 ± 4 | 3.1 ± 0.2 |
| G-CaMP7·X· | 36.6 ± 4.1 | 243 ± 14 | 2.7 ± 0.4 |
| G-CaMP8·X· | 37.5 ± 3.6 | 200 ± 1 | 2.2 ± 0.2 |

·X·see PLOS One, 2012, 7, e51286.

TABLE 2

|  | Kd (nM) | Hill coefficient | $F_{max}/F_{min}$ |
|---|---|---|---|
| R-CaMP2_LLA | 97 ± 10 | 1.1 ± 0.1 | 5.1 ± 0.3 |
| X-CaMPBlue | 71 ± 3 | 1.3 ± 0.1 | 7.2 ± 0.7 |
| X-CaMPGreen | 128 ± 5 | 1.3 ± 0.1 | 5.9 ± 0.1 |
| X-CaMPYellow | 182 ± 3 | 1.6 ± 0.0 | 30.5 ± 1.8 |

R-CaMP2 and R-GECO2L have Hill coefficients close to 1 (Table 1). These Hill coefficients are substantially equal to those of chemically synthesized calcium indicators such as 0 GB-1 (J. Neurosci., 2008, 7399-7411). This is clearly distinct from the fact that many of the existing fluorescent calcium indicator proteins have Hill coefficients of 2 or more (Table 1).

To verify the utility of R-CaMP2 in brain tissue, R-CaMP2 was transfected into neurons in the layer ⅔ of the barrel field by intrauterus electroporation (J. Neurosci., 2009, 29, 13720-13729), and acute slices were prepared in adult mice. Using a titanium sapphire laser for excitation, fast (near 700 Hz) two-photon line-scan $Ca^{2+}$ imaging combined with whole-cell patch-clamp was performed in the soma and proximal dendrites of R-CaMP2-expressing neurons. Similar experiments were also performed for R-CaMP2_LLA and X-CaMPGreen.

Figure 12:
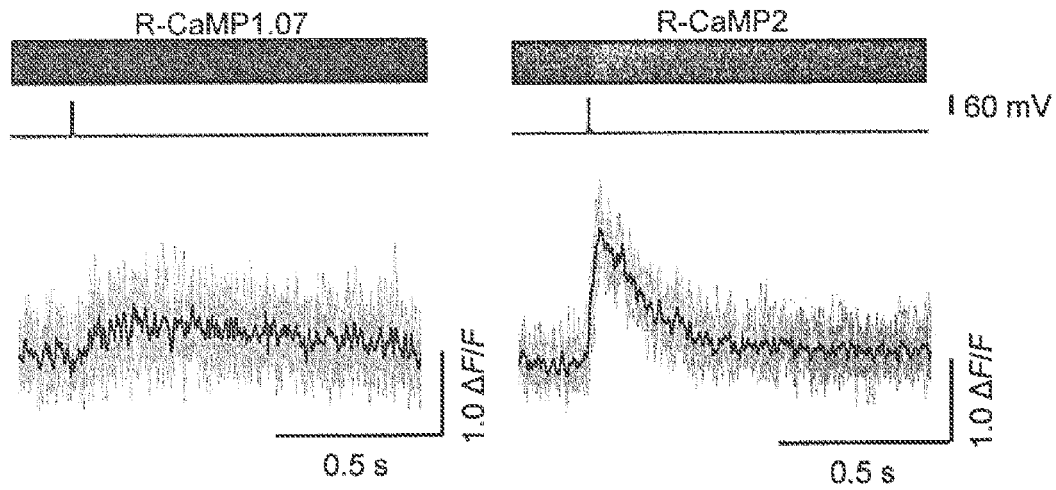
FIG. 12 shows a comparison between R-CaMP2 and R-CaMP1.07 in fluorescence changes (ΔF/F) in response to action potentials in pyramidal cells in the layer ⅔ of the barrel field in acute slices (n=10 cells).
Figure 13A:
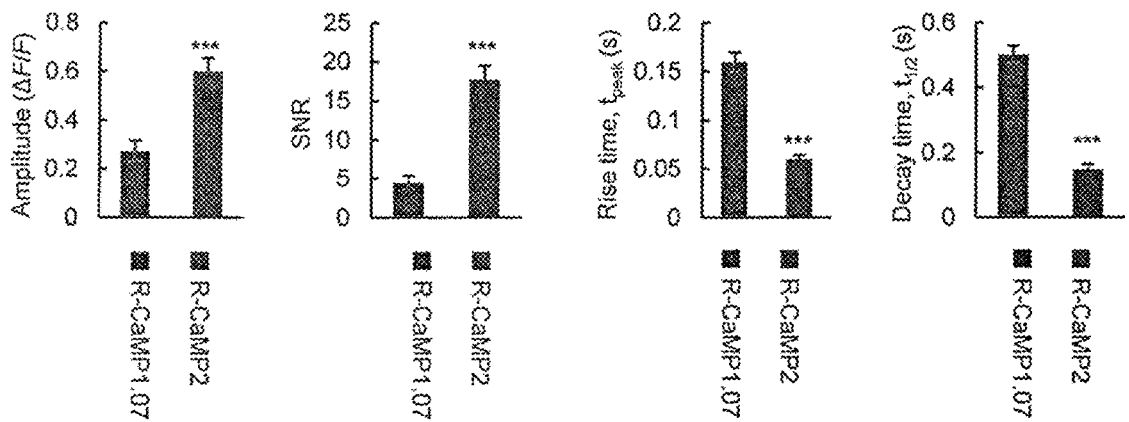
FIG. 13A shows amplitudes, SNRs, rise times, and decay time constants of single action potential-evoked $Ca^{2+}$ responses in acute slices.
Figure 13B:
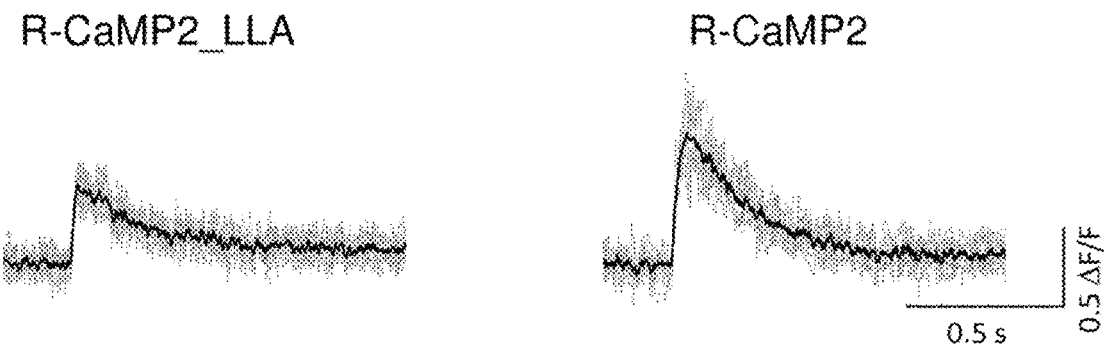
FIG. 13B shows a comparison between R-CaMP2_LLA and R-CaMP2 in fluorescence changes (ΔF/F) in response to action potentials in pyramidal cells in the layer ⅔ of the barrel field in acute slices (n=10 cells).
Figure 13C:
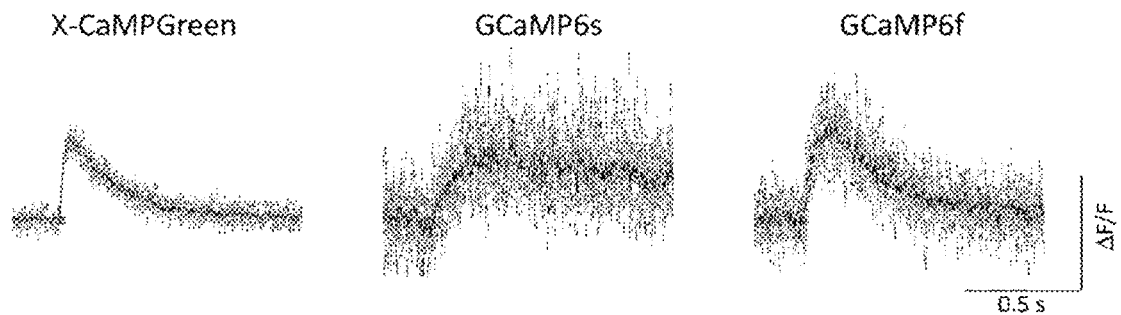
FIG. 13C shows fluorescence changes (ΔF/F) of X-CaMPGreen in response to action potentials in pyramidal cells in the layer ⅔ of the barrel field in acute slices (n=10 cells), in comparison with those of the calcium indicator proteins, GCaMP6s and GCaMP6f, according to known techniques.

In line with the results for the primary cultured hippocampal neurons, ΔF/F response amplitudes generated by single depolarizing current injection were significantly larger in R-CaMP2-expressing neurons than in R-CaMP1.07-expressing neurons (FIGS. 12 and 13). R-CaMP2 showed several-fold improvements over R-CaMP1.07 (FIG. 13A) in terms of signal-to-noise ratio (SNR) (4.0-fold higher at maximum), rise time (2.6-fold faster at maximum), and decay time constant (3.4-fold faster at maximum). R-CaMP2_LLA showed a rise time even faster than that of R-CaMP2 (FIG. 13B). Moreover, X-CaMPGreen showed a rise time faster than those of conventional green fluorescent calcium indicator proteins, GCaMP6s and GCaMP6f (Nature, 2013, Vol. 499, p. 295-300) (FIG. 13C). Note that GCaMP6s and GCaMP6f are calcium sensors containing the M13 sequence.

Figure 14:
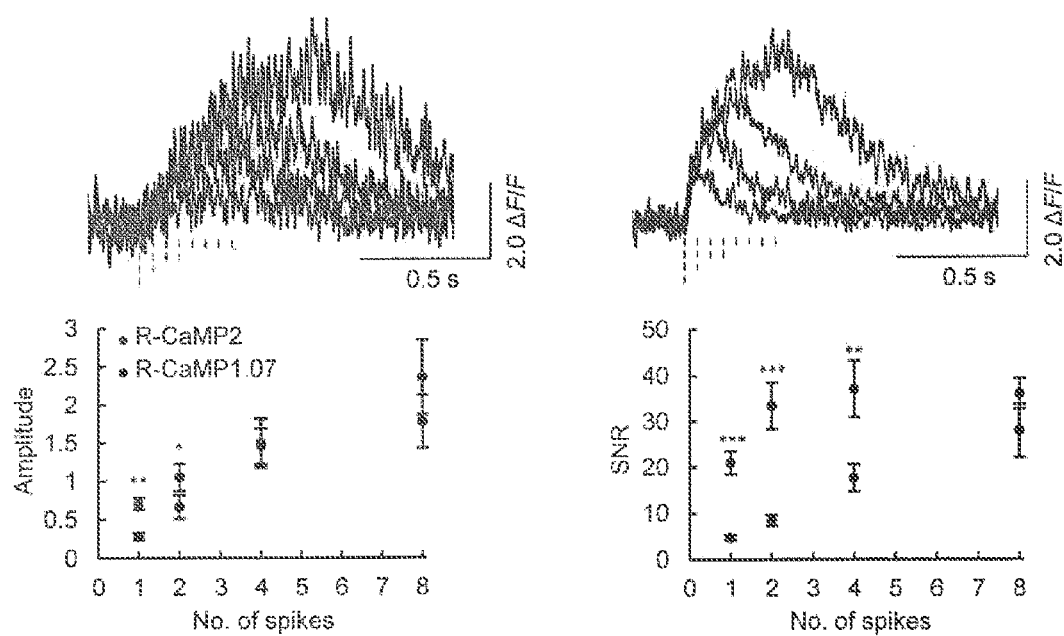
FIG. 14 shows representative traces (top) and average performance (bottom) of R-CaMP1.07- and R-CaMP2-expressing neurons in response to one, two, four, and eight spikes at 20 Hz, in pyramidal cells in the layer ⅔ of the barrel field in acute slices.
Figure 15C:
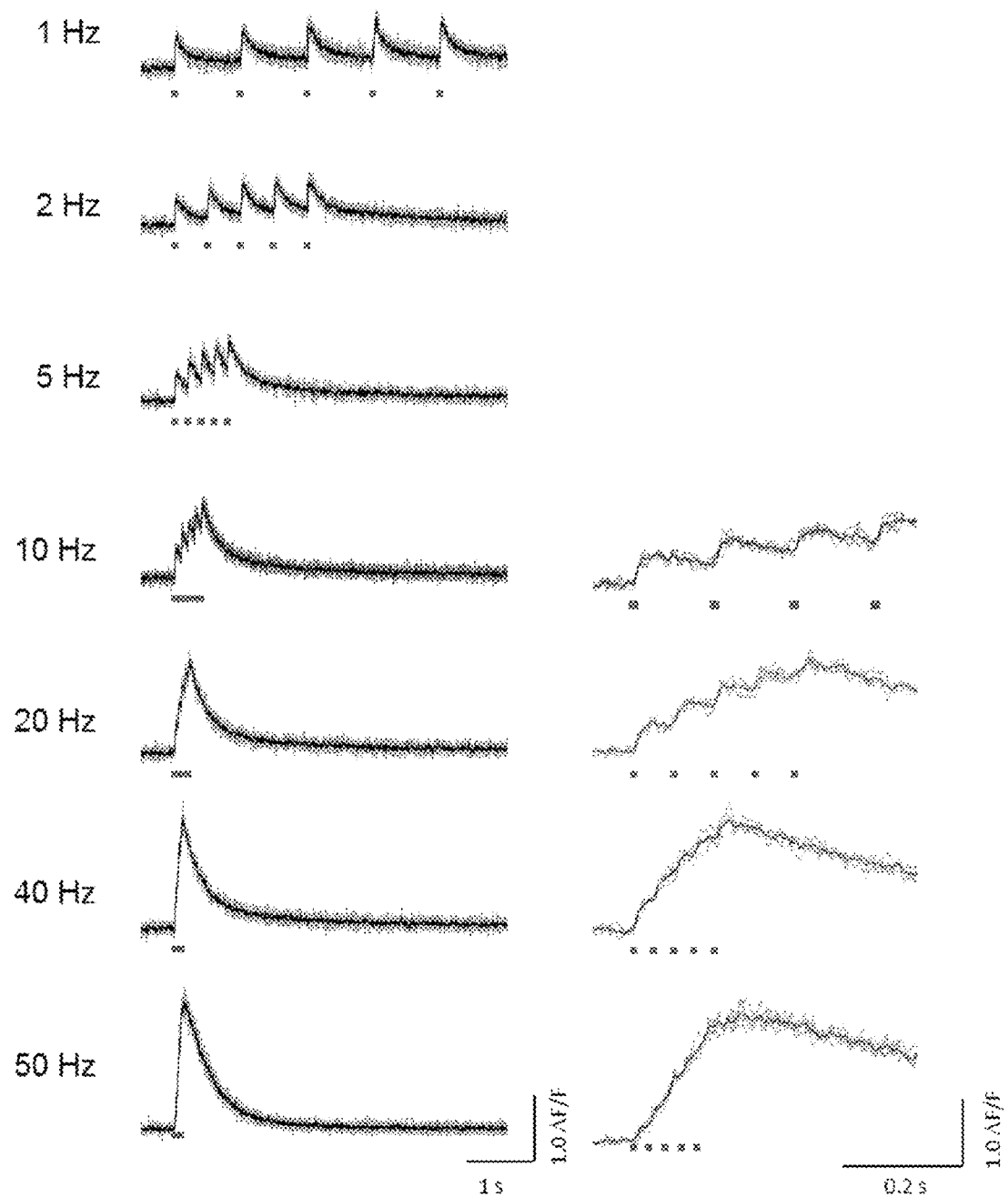
FIG. 15C shows single-trial responses of R-CaMP2_LLA when clamped to five spikes and stimulated at difference frequencies in pyramidal cells in the layer ⅔ of the barrel field in acute slices.
Figure 15D:
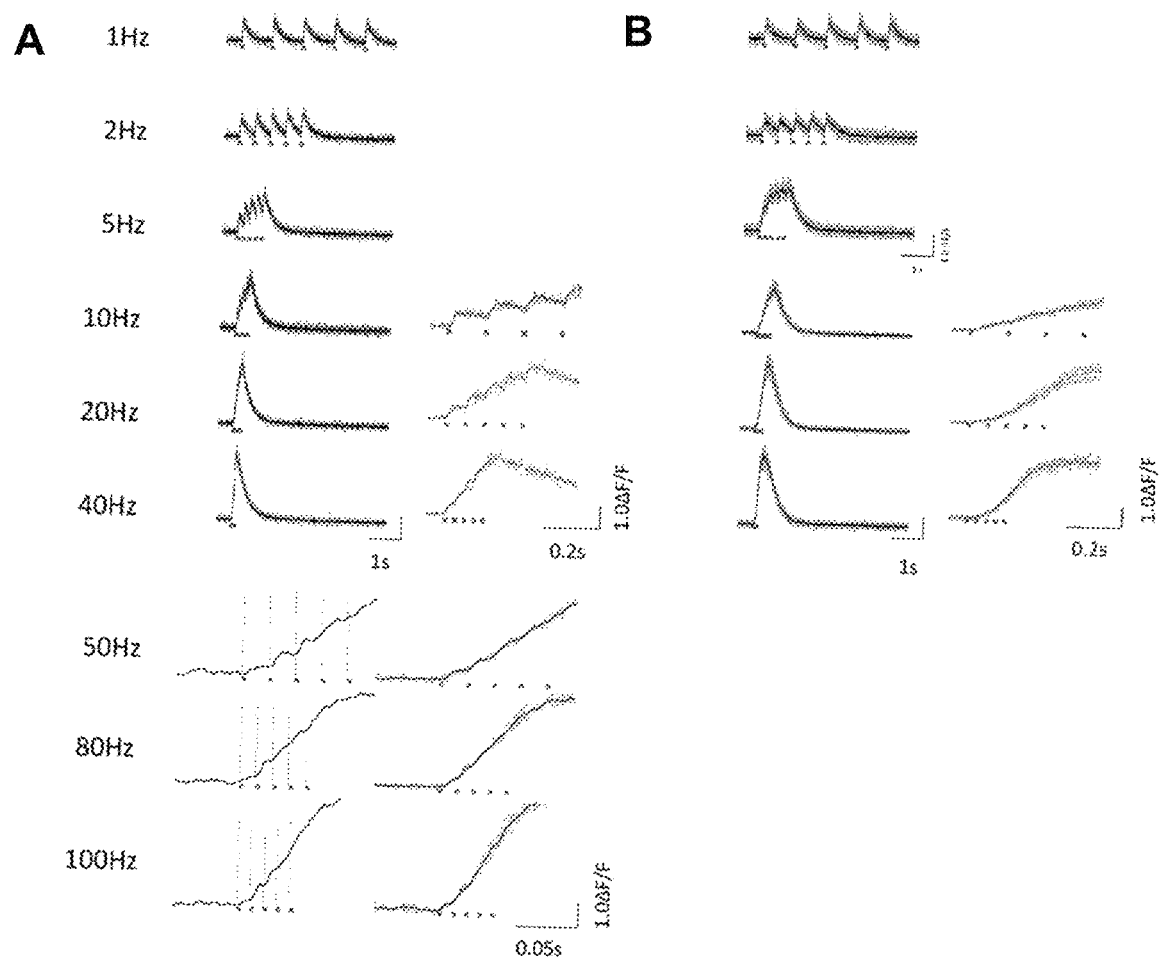
FIG. 15D shows single-trial responses of X-CaMPGreen when clamped to five spikes and stimulated at difference frequencies in pyramidal cells in the layer ⅔ of the barrel field in acute slices (A); and shows the results for GCaMP6f for comparison (B).

In agreement with these improved parameters, R-CaMP2 showed improvements in ΔF/F amplitude and SNR up to a maximum four pulses of successive pulses of current injection (FIG. 14). Moreover, successive action potentials at 20 to 40 Hz could be distinguished even with a single trial (FIG. 15B). Under the same experimental conditions, $Ca^{2+}$ signals recorded from R-CaMP1.07-expressing neurons showed larger baseline noise and a slower rise time, and thus, action potentials could only be distinguished up to pulses with a frequency of 5 Hz (FIG. 15A). R-CaMP2_LLA followed stimulation at frequencies even higher than those for R-CaMP2, and had a resolution at up to 50 Hz (FIG. 15-2). Moreover, X-CaMPGreen followed even ultra-fast frequencies of 80 to 100 Hz (FIG. 15-3).

Figure 16:
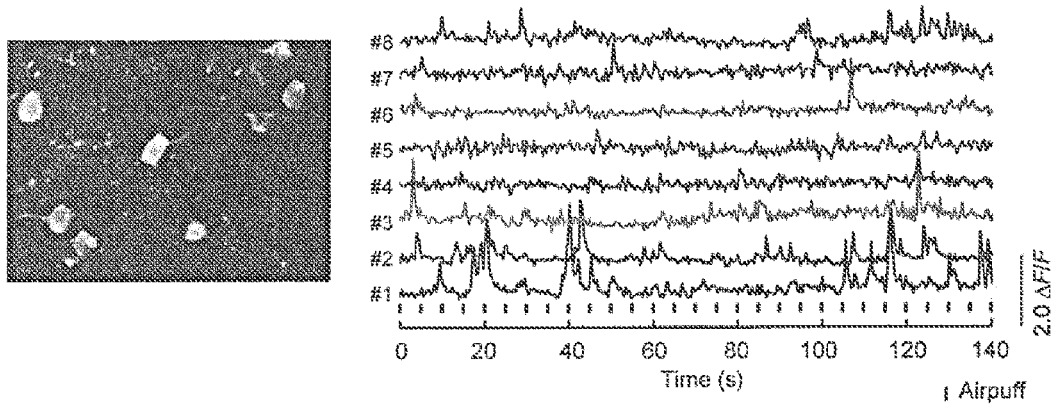
FIG. 16 shows the results obtained by recording air-puff whisker stimulation-evoked $Ca^{2+}$ transients in a plurality of neurons by in vivo imaging.

In vivo $Ca^{2+}$ imaging was performed in neurons in the layer ⅔ of the barrel field of anesthetized head-fixed mice. Under conditions in which about 30 to 60% of pyramidal neurons in the layer ⅔ were labeled, spontaneous $Ca^{2+}$ spikes could be reliably recorded (FIG. 16). The representation of tactile information is encoded by sparse neurons (Neuron, 2010, 67, 1048-1061, Neuron, 2013, 78, 28-48, Trends Neurosci., 2012, 35, 345-355). In agreement with this, air-puff stimulation on the whiskers evoked $Ca^{2+}$ transients in only a limited number of cells. Moreover, active neurons that showed stimulus-correlated activity for R-CaMP2-based $Ca^{2+}$ transients showed evoked responses upon successive air-puff stimuli. That is, active neurons responsive to sensory stimulation in the barrel field could be identified.

Figure 17:
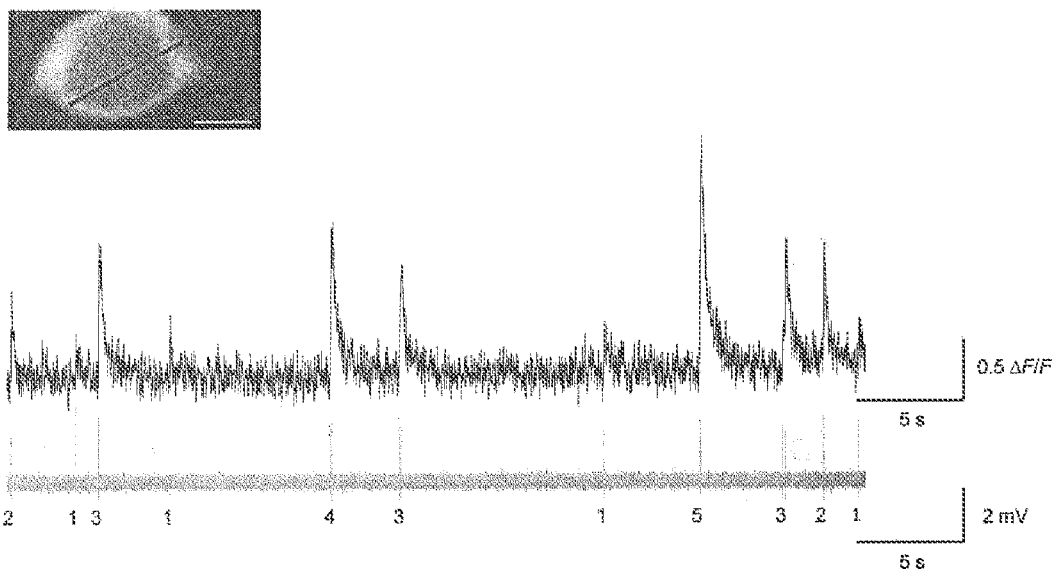
FIG. 17 shows representative traces of simultaneous recording of $Ca^{2+}$ transients (top) and action potentials (bottom) in R-CaMP2-expressing neocortical neurons in vivo; the number of spikes in each burst is shown under the traces; scale bars: 5 μm.
Figure 18:
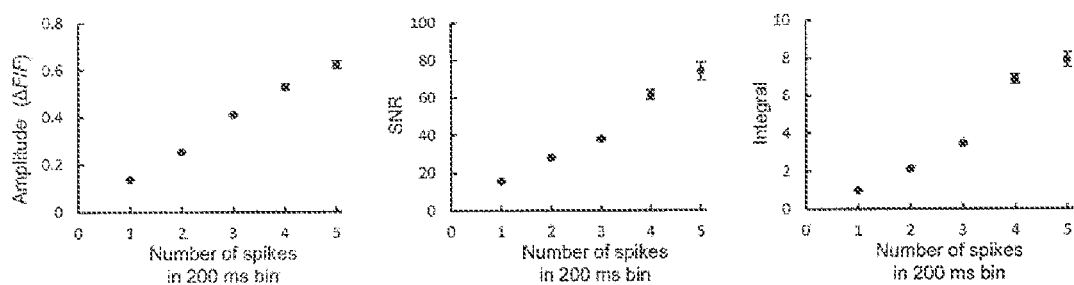
FIG. 18 shows amplitudes, SNRs, and temporal integral values of $Ca^{2+}$ transients evoked by the number of action potentials in a 200 ms bin in in vivo neocortical neurons (one, two, three, four, and five action potentials detected n=254, 115, 45, 26, and 13 events. Nine cells from n=7 mice).

To examine in vivo recording resolution, fast line scan $Ca^{2+}$ imaging was performed simultaneously with loose-seal cell-attached electrical recording (FIG. 17). Spontaneous action potentials showed an approximately linear increase in each of the responses of SNR, amplitude, and temporal integral of the amplitude up to five pulses (FIG. 18). The foregoing results reveal that in terms of rise and decay time kinetics of $Ca^{2+}$ transients evoked by single action potentials in vivo, R-CaMP2 is comparable to a previously reported green fluorescent calcium indicator protein such as GCaMP6f (Nature, 2013, 499, 295-300) or fast-GCaMP (Nat. Commun., 2013, 4, 2170) having fast kinetics.

SEQUENCE LISTING FREE TEXT

SEQ ID NO: 1: Base sequence of a nucleotide sequence encoding one coding derivative of a ckkap sequence (ckkap α) derived from the α subunit of CaMKK.

SEQ ID NO: 2: Base sequence of a nucleotide sequence encoding one coding derivative of a ckkap sequence (ckkap β) derived from the β subunit of CaMKK.

SEQ ID NO: 3: Base sequence of a nucleotide sequence encoding one coding derivative of a ckkap sequence, ckkap-WL.

SEQ ID NO: 4: Amino acid sequence of one coding derivative of the ckkap sequence (ckkap α) derived from the α subunit of CaMKK.

SEQ ID NO: 5: Amino acid sequence of one coding derivative of the ckkap sequence (ckkap β) derived from the β subunit of CaMKK.

SEQ ID NO: 6: Amino acid sequence of one coding derivative of a ckkap sequence, ckkap-WL.

SEQ ID NO: 7: Base sequence of a nucleotide sequence encoding a CaM sequence of R-CaMP2.

SEQ ID NO: 8: Base sequence of a nucleotide sequence encoding a CaM sequence of R-GECO2L.

SEQ ID NO: 9: Amino acid sequence of the CaM sequence of R-CaMP2.

SEQ ID NO: 10: Amino acid sequence of the CaM sequence of R-GECO2L.

SEQ ID NO: 11: Amino acid sequence of R-CaMP2.

SEQ ID NO: 12: Base sequence of a nucleotide sequence encoding R-CaMP2.

SEQ ID NO: 13: Amino acid sequence of R-GECO2L.

SEQ ID NO: 14: Base sequence of a nucleotide sequence encoding R-GECO2L.

SEQ ID NO: 15: Amino acid sequence of one coding derivative of a ckkap sequence, ckkap-WL2.

SEQ ID NO: 16: Amino acid sequence of one coding derivative of a ckkap sequence, ckkap-WL3.

SEQ ID NO: 17: Amino acid sequence of one coding derivative of a ckkap sequence, ckkap-WL4.

SEQ ID NO: 18: Amino acid sequence of one coding derivative of a ckkap sequence, ckkap-WL5.

SEQ ID NO: 19: Amino acid sequence of one coding derivative of a ckkap sequence, ckkap-WL6.

What is claimed is:

1. A DNA comprising:
a first nucleotide sequence encoding a calmodulin-binding sequence (ckkap sequence) of calcium/calmodulin-dependent protein kinase kinase, wherein the ckkap sequence is the amino acid sequence set forth in SEQ ID NO: 6; and
a second nucleotide sequence encoding a calcium-binding sequence (CaM sequence) of calmodulin,
wherein one of the first or second nucleotide sequence is linked to a 5' end of a nucleotide sequence encoding a fluorescent protein, and the other of the first or second nucleotide sequence is linked to a 3' end of the nucleotide sequence encoding the fluorescent protein.

2. The DNA according to claim 1, wherein
the first nucleotide sequence and the second nucleotide sequence are each linked to the nucleotide sequence encoding the fluorescent protein via a nucleotide sequence encoding an amino acid linker.

3. The DNA according to claim 2, wherein
the first nucleotide sequence is linked to the 5' end of the nucleotide sequence encoding the fluorescent protein, and the second nucleotide sequence is linked to the 3' end of the nucleotide sequence encoding the fluorescent protein,
the first nucleotide sequence and the nucleotide sequence encoding the fluorescent protein are linked via a nucleotide sequence encoding an amino acid linker A, and
the nucleotide sequence encoding the fluorescent protein and the second nucleotide sequence are linked via a nucleotide sequence encoding an amino acid linker B, and wherein
the amino acid linker A is (-Pro-Val-) and the amino acid linker is B (-Thr-Arg-).

4. A vector comprising the DNA according to claim 1.

5. A protein comprising:
a first polypeptide sequence comprising a calmodulin-binding sequence (ckkap sequence) of calcium/calmodulin-dependent protein kinase kinase, wherein the ckkap sequence is the amino acid sequence set forth in SEQ ID NO: 6; and
a second polypeptide sequence comprising a calcium-binding sequence (CaM sequence) of calmodulin,
wherein one of the first or second polypeptide sequence is linked to an N-terminus of a polypeptide sequence comprising a fluorescent protein, and the other of the first or second polypeptide sequence is linked to a C-terminus of the polypeptide sequence comprising the fluorescent protein.

6. The protein according to claim 5, wherein
the first polypeptide sequence and the second polypeptide sequence are each linked to the polypeptide sequence comprising the fluorescent protein via an amino acid linker.

7. The protein according to claim 6, wherein
the first polypeptide sequence is linked to the N-terminus of the polypeptide sequence comprising the fluorescent protein, and the second polypeptide sequence is linked to the C-terminus of the polypeptide sequence comprising the fluorescent protein,
the first polypeptide sequence and the polypeptide sequence comprising the fluorescent protein are linked via an amino acid linker A, and
the polypeptide sequence comprising the fluorescent protein and the second polypeptide sequence are linked via an amino acid linker B, and wherein
the amino acid linker A is (-Pro-Val-) and the amino acid linker B is (-Thr-Arg-).

8. A calcium indicator reagent for measuring an action potential in a cell and/or imaging a calcium ion in a cell, the reagent comprising:
(i) a DNA comprising a first nucleotide sequence encoding a calmodulin-binding sequence (ckkap sequence)

of calcium/calmodulin-dependent protein kinase kinase, wherein the ckkap sequence is the amino acid sequence set forth in SEQ ID NO: 6, and a second nucleotide sequence encoding a calcium-binding sequence (CaM sequence) of calmodulin, wherein one of the first or second nucleotide sequence is linked to a 5' end of a nucleotide sequence encoding a fluorescent protein, and the other of the first or second nucleotide sequence is linked to a 3' end of the nucleotide sequence encoding the fluorescent protein, or (ii) a vector comprising the DNA of (i).

9. The reagent according to claim 8, wherein the cell is a neuron.

10. A vector comprising the DNA according to claim 2.

11. A vector comprising the DNA according to claim 3.

* * * * *

SEQUENCE LISTING

```
<160> NUMBER OF SEQ ID NOS: 19

<210> SEQ ID NO 1
<211> LENGTH: 78
<212> TYPE: DNA
<213> ORGANISM: Rattus rattus

<400> SEQUENCE: 1
gtcaagctca tccccagctg gaccactgtg atcctggtca agtctatgct gagaaagcgt      60
tcctttggaa acccattt                                                   78

<210> SEQ ID NO 2
<211> LENGTH: 78
<212> TYPE: DNA
<213> ORGANISM: Rattus rattus
```

<400> SEQUENCE: 2
gtcaaacaca ttcccagcct ggcaactgtg atcctagtga agaccatgat tcggaaacgg    60
tcttttggga acccattt                                                  78

<210> SEQ ID NO 3
<211> LENGTH: 78
<212> TYPE: DNA
<213> ORGANISM: Artificial Sequence
<220> FEATURE:
<223> OTHER INFORMATION: ckkap-WL

<400> SEQUENCE: 3
gtcaaacaca ttcccagcct ggcaactgtg atcctagtga agaccatgat tcggaaacgg    60
tcttttggga acccattt                                                  78

<210> SEQ ID NO 4
<211> LENGTH: 26
<212> TYPE: PRT
<213> ORGANISM: Rattus rattus

<400> SEQUENCE: 4

Val Lys Leu Ile Pro Ser Trp Thr Thr Val Ile Leu Val Lys Ser Met
1               5                   10                  15

Leu Arg Lys Arg Ser Phe Gly Asn Pro Phe
            20                  25

<210> SEQ ID NO 5
<211> LENGTH: 26
<212> TYPE: PRT
<213> ORGANISM: Rattus rattus

<400> SEQUENCE: 5

Val Lys His Ile Pro Ser Leu Ala Thr Val Ile Leu Val Lys Thr Met
1               5                   10                  15

Ile Arg Lys Arg Ser Phe Gly Asn Pro Phe
            20                  25

<210> SEQ ID NO 6
<211> LENGTH: 26
<212> TYPE: PRT
<213> ORGANISM: Artificial Sequence
<220> FEATURE:
<223> OTHER INFORMATION: ckkap-WL

<400> SEQUENCE: 6

Val Lys Leu Ile Pro Ser Leu Thr Thr Val Ile Leu Val Lys Ser Met
1               5                   10                  15

Leu Arg Lys Arg Ser Phe Gly Asn Pro Phe
            20                  25

<210> SEQ ID NO 7
<211> LENGTH: 441
<212> TYPE: DNA
<213> ORGANISM: Artificial Sequence
<220> FEATURE:
<223> OTHER INFORMATION: CaM sequence of R-CaMP2

<400> SEQUENCE: 7
gaccaactga ctgaagagca gatcgcagaa tttaaagagg ctttctccct atttgacaag    60
gacggggatg ggacaataac aaccaaggag ctggggacgg tgatgcggtc tctggggcag   120

```
aaccccacag aagcagagct gcaggacatg atcaatgaag tagatgccga cggtgatggc    180
acattcgact ccctgagtt cctgacaatg atggcaagaa aaatgagcta cagagacacc    240
gaagaagaaa ttagagaagc gttccgtgtg tttgataagg atggcaatgg ctacatcggc   300
gcagcagagc ttcgccacgt gatgacagac cttggagaga agttaacaga tgaagaggtt   360
gatgaaatga tcagggtggc agacatcgat ggggatggtc agtaaactg cgaagagttt    420 gtacaaatga tgacagcgaa g                                              441
```

<210> SEQ ID NO 8
<211> LENGTH: 441
<212> TYPE: DNA
<213> ORGANISM: Artificial Sequence
<220> FEATURE:
<223> OTHER INFORMATION: CaM sequence of R-GECO2L

<400> SEQUENCE: 8

```
gaccaactga ctgaagagca gatcgcagaa tttaaagagg ctttctccct atttgacaag   60
gacggggatg ggacgataac aaccaaggag ctggggacgg tgatgcggtc tctggggcag   120
aaccccacag aagcagagct gcaggacatg atcaatgaag tagatgccga cggtgacggc   180
acattcgact ccctgagtt cctgacgatg atggcaagaa aaatgagcta cagagacacc    240
gaagaagaaa ttagagaagc gttccgcgtg tttgataagg acggcaatgg ctacatcggc   300
gcagcagagc ttcgccacgt gatgacagac cttggagaga agttaacaga tgaggaggtt   360
gatgaaatga tcagggtagc agacatcgat ggggatggtc agtaaactg cgaagagttt    420 gtacaaatga tgacagcgaa g                                              441
```

<210> SEQ ID NO 9
<211> LENGTH: 147
<212> TYPE: PRT
<213> ORGANISM: Artificial Sequence
<220> FEATURE:
<223> OTHER INFORMATION: CaM sequence of R-CaMP2

<400> SEQUENCE: 9

```
Asp Gln Leu Thr Glu Glu Gln Ile Ala Glu Phe Lys Glu Ala Phe Ser
1               5                   10                  15

Leu Phe Asp Lys Asp Gly Asp Gly Thr Ile Thr Thr Lys Glu Leu Gly
            20                  25                  30

Thr Val Met Arg Ser Leu Gly Gln Asn Pro Thr Glu Ala Glu Leu Gln
        35                  40                  45

Asp Met Ile Asn Glu Val Asp Ala Asp Gly Asp Gly Thr Phe Asp Phe
    50                  55                  60

Pro Glu Phe Leu Thr Met Met Ala Arg Lys Met Ser Tyr Arg Asp Thr
65                  70                  75                  80

Glu Glu Glu Ile Arg Glu Ala Phe Arg Val Phe Asp Lys Asp Gly Asn
                85                  90                  95

Gly Tyr Ile Gly Ala Ala Glu Leu Arg His Val Met Thr Asp Leu Gly
            100                 105                 110

Glu Lys Leu Thr Asp Glu Glu Val Asp Glu Met Ile Arg Val Ala Asp
        115                 120                 125

Ile Asp Gly Asp Gly Gln Val Asn Tyr Glu Glu Phe Val Gln Met Met
    130                 135                 140

Thr Ala Lys
145
```

<210> SEQ ID NO 10
<211> LENGTH: 147
<212> TYPE: PRT
<213> ORGANISM: Artificial Sequence
<220> FEATURE:
<223> OTHER INFORMATION: CaM sequence of R-GECO2L

<400> SEQUENCE: 10

Asp Gln Leu Thr Glu Glu Gln Ile Ala Glu Phe Lys Glu Ala Phe Ser
1               5                   10                  15

Leu Phe Asp Lys Asp Gly Asp Gly Thr Ile Thr Thr Lys Glu Leu Gly
            20                  25                  30

Thr Val Met Arg Ser Leu Gly Gln Asn Pro Thr Glu Ala Glu Leu Gln
        35                  40                  45

Asp Met Ile Asn Glu Val Asp Ala Asp Gly Asp Gly Thr Phe Asp Phe
    50                  55                  60

Pro Glu Phe Leu Thr Met Met Ala Arg Lys Met Ser Tyr Arg Asp Thr
65                  70                  75                  80

Glu Glu Glu Ile Arg Glu Ala Phe Arg Val Phe Asp Lys Asp Gly Asn
                85                  90                  95

Gly Tyr Ile Gly Ala Ala Glu Leu Arg His Val Met Thr Asn Leu Gly
            100                 105                 110

Glu Lys Leu Thr Asp Glu Glu Val Asp Glu Met Ile Arg Val Ala Asp
        115                 120                 125

Ile Asp Gly Asp Gly Gln Val Asn Tyr Glu Glu Phe Val Gln Met Met
    130                 135                 140

Thr Ala Lys
145

<210> SEQ ID NO 11
<211> LENGTH: 492
<212> TYPE: PRT
<213> ORGANISM: Artificial Sequence
<220> FEATURE:
<223> OTHER INFORMATION: R-CaMP2

<400> SEQUENCE: 11

Met Gly Ser His His His His His His Gly Met Ala Ser Met Thr Gly
1               5                   10                  15

Gly Gln Gln Met Gly Arg Asp Leu Tyr Asp Asp Asp Asp Lys Asp Leu
            20                  25                  30

Ala Thr Met Val Asp Val Lys Leu Ile Pro Ser Leu Thr Thr Val Ile
        35                  40                  45

Leu Val Lys Ser Met Leu Arg Lys Arg Ser Phe Gly Asn Pro Phe Pro
    50                  55                  60

Val Val Ser Glu Arg Met Tyr Pro Glu Asp Gly Ala Leu Lys Ser Glu
65                  70                  75                  80

Ile Lys Lys Gly Leu Arg Leu Lys Asp Gly Gly His Tyr Ala Ala Glu
                85                  90                  95

Val Lys Thr Thr Tyr Lys Ala Lys Lys Pro Val Gln Leu Pro Gly Ala
            100                 105                 110

Tyr Ile Val Asp Ile Lys Leu Asp Ile Val Ser His Asn Glu Asp Tyr
        115                 120                 125

Thr Ile Val Glu Gln Cys Glu Arg Ala Glu Gly Arg His Ser Thr Gly
    130                 135                 140

Gly Met Asp Glu Leu Tyr Lys Gly Gly Thr Gly Gly Ser Leu Val Ser
145                 150                 155                 160

```
Lys Gly Glu Glu Asp Asn Met Ala Ile Ile Lys Glu Phe Met Arg Phe
                165                 170                 175
Lys Val His Met Glu Gly Ser Val Asn Gly His Glu Phe Glu Ile Glu
            180                 185                 190
Gly Glu Gly Glu Gly Arg Pro Tyr Glu Ala Phe Gln Thr Ala Lys Leu
        195                 200                 205
Val Val Val Lys Gly Gly Pro Leu Pro Phe Ala Trp Asp Ile Leu Ser
210                 215                 220
Pro Gln Phe Met Tyr Gly Ser Lys Ala Tyr Ile Lys His Pro Ala Asp
225                 230                 235                 240
Ile Pro Asp Tyr Phe Lys Leu Ser Phe Pro Glu Gly Phe Arg Trp Glu
                245                 250                 255
Arg Val Met Asn Phe Glu Asp Gly Gly Ile Ile His Val Asn Gln Asp
            260                 265                 270
Ser Ser Leu Gln Asp Gly Val Phe Ile Tyr Lys Val Lys Leu Arg Gly
        275                 280                 285
Thr Asn Phe Pro Pro Asp Gly Pro Val Met Gln Lys Lys Thr Met Gly
290                 295                 300
Trp Glu Ala Thr Arg Asp Gln Leu Thr Glu Glu Gln Ile Ala Glu Phe
305                 310                 315                 320
Lys Glu Ala Phe Ser Leu Phe Asp Lys Asp Gly Asp Gly Thr Ile Thr
                325                 330                 335
Thr Lys Glu Leu Gly Thr Val Met Arg Ser Leu Gly Gln Asn Pro Thr
            340                 345                 350
Glu Ala Glu Leu Gln Asp Met Ile Asn Glu Val Asp Ala Asp Gly Asp
        355                 360                 365
Gly Thr Phe Asp Phe Pro Glu Phe Leu Thr Met Met Ala Arg Lys Met
370                 375                 380
Ser Tyr Arg Asp Thr Glu Glu Ile Arg Glu Ala Phe Arg Val Phe
385                 390                 395                 400
Asp Lys Asp Gly Asn Gly Tyr Ile Gly Ala Ala Glu Leu Arg His Val
                405                 410                 415
Met Thr Asp Leu Gly Glu Lys Leu Thr Asp Glu Glu Val Asp Glu Met
            420                 425                 430
Ile Arg Val Ala Asp Ile Asp Gly Asp Gly Gln Val Asn Tyr Glu Glu
        435                 440                 445
Phe Val Gln Met Met Thr Ala Lys Gly Gly Thr Gly Gly Ser Gly
450                 455                 460
Gly Gly Gly Gly Glu Phe Pro Val Lys Gln Thr Leu Asn Phe Asp
465                 470                 475                 480
Leu Leu Lys Leu Ala Gly Asp Val Glu Ser Asn Pro
                485                 490
```

<210> SEQ ID NO 12
<211> LENGTH: 1479
<212> TYPE: DNA
<213> ORGANISM: Artificial Sequence
<220> FEATURE:
<223> OTHER INFORMATION: R-CaMP2

<400> SEQUENCE: 12
atgggttctc atcatcatca tcatcatggt atggctagca tgactggtgg acagcaaatg      60
ggtcgggatc tgtacgacga tgacgataag gatctcgcca ccatggtcga cgtcaagctc     120
atccccagcc tgaccactgt gatcctggtc aagtctatgc tgagaaagcg ttcctttgga     180

```
aacccatttc ccgtggtttc cgagcggatg taccccgagg acggcgccct gaagagcgag    240
atcaagaagg ggctgaggct gaaggacggc ggccactacg ccgccgaggt caagaccacc    300
tacaaggcca agaagcccgt gcagctgccc ggcgcctaca tcgtggacat caagttggac    360
atcgtgtccc acaacgagga ctacaccatc gtggaacagt gcgaacgcgc cgagggccgc    420
cactccaccg gcggcatgga cgagctgtac aagggcggta ccggagggag cctggtgagc    480
aagggcgagg aggacaacat ggccatcatc aaggagttca tgcgcttcaa ggtgcacatg    540
gagggctccg tgaacggcca cgagttcgag atcgagggcg agggcgaggg ccgcccctac    600
gaggcctttc agaccgctaa gcttgtcgtc gttaagggtg gtcctctgcc cttcgcctgg    660
gacatcctgt cccctcagtt catgtacggc tccaaggcct acattaagca cccagccgac    720
atccccgact acttcaagct gtccttcccc gagggcttca ggtgggagcg cgtgatgaac    780
ttcgaggacg gcggcattat tcacgttaac caggactcct ccctgcaaga cggcgtgttc    840
atctacaagg tgaagctgcg cggcaccaac ttccccccccg acggcccgt aatgcagaag    900
aagaccatgg gctgggaggc cacccgcgac caactgactg aagagcagat cgcagaattt    960
aaagaggctt tctccctatt tgacaaggac ggggatggga caataacaac caaggagctg   1020
gggacggtga tgcggtctct ggggcagaac cccacagaag cagagctgca ggacatgatc   1080
aatgaagtag atgccgacgg tgatggcaca ttcgacttcc ctgagttcct gacaatgatg   1140
gcaagaaaaa tgagctacag agacaccgaa gaagaaatta gagaagcgtt ccgtgtgttt   1200
gataaggatg gcaatggcta catcggcgca gcagagcttc gccacgtgat gacagacctt   1260
ggagagaagt taacagatga agaggttgat gaaatgatca gggtggcaga catcgatggg   1320
gatggtcagg taaactacga agagtttgta caaatgatga cagcgaaggg cggagggact   1380
ggaggcagtg gtggtggtgg tggtggtgaa ttcccggtga acagactttt gaattttgac   1440
cttctcaagt tggcgggaga cgtggagtcc aacccatag                           1479
```

<210> SEQ ID NO 13
<211> LENGTH: 422
<212> TYPE: PRT
<213> ORGANISM: Artificial Sequence
<220> FEATURE:
<223> OTHER INFORMATION: R-GECO2L

<400> SEQUENCE: 13

```
Met Val Asp Val Lys Leu Ile Pro Ser Leu Thr Thr Val Ile Leu Val
1               5                   10                  15

Lys Ser Met Leu Arg Lys Arg Ser Phe Gly Asn Pro Phe Pro Val Val
            20                  25                  30

Ser Glu Arg Met Tyr Pro Glu Asp Gly Ala Leu Lys Ser Glu Ile Lys
        35                  40                  45

Lys Gly Leu Arg Leu Lys Asp Gly Gly His Tyr Ala Ala Glu Val Lys
    50                  55                  60

Thr Thr Tyr Lys Ala Lys Lys Pro Val Gln Leu Pro Gly Ala Tyr Ile
65                  70                  75                  80

Val Asp Ile Lys Leu Asp Ile Val Ser His Asn Glu Asp Tyr Thr Ile
                85                  90                  95

Val Glu Gln Cys Glu Arg Ala Glu Gly Arg His Ser Thr Gly Gly Met
            100                 105                 110

Asp Glu Leu Tyr Lys Gly Gly Thr Gly Gly Ser Leu Val Ser Lys Gly
        115                 120                 125

Glu Glu Asp Asn Met Ala Ile Ile Lys Glu Phe Met Arg Phe Lys Val
```

His Met Glu Gly Ser Val Asn Gly His Glu Phe Glu Ile Gly Glu
145                 150                 155                 160

Gly Glu Gly Arg Pro Tyr Glu Ala Phe Gln Thr Ala Lys Leu Lys Val
            165                 170                 175

Thr Lys Gly Gly Pro Leu Pro Phe Ala Trp Asp Ile Leu Ser Pro Gln
        180                 185                 190

Phe Met Tyr Gly Ser Lys Ala Tyr Ile Lys His Pro Ala Asp Ile Pro
            195                 200                 205

Asp Tyr Phe Lys Leu Ser Phe Pro Glu Gly Phe Arg Trp Glu Arg Val
        210                 215                 220

Met Asn Phe Glu Asp Gly Gly Ile Ile His Val Asn Gln Asp Ser Ser
225                 230                 235                 240

Leu Gln Asp Gly Val Phe Ile Tyr Lys Val Lys Leu Arg Gly Thr Asn
                245                 250                 255

Phe Pro Pro Asp Gly Pro Val Met Gln Lys Lys Thr Met Gly Trp Glu
            260                 265                 270

Ala Gly Arg Asp Gln Leu Thr Glu Glu Gln Ile Ala Glu Phe Lys Glu
        275                 280                 285

Ala Phe Ser Leu Phe Asp Lys Asp Gly Asp Gly Thr Ile Thr Thr Lys
    290                 295                 300

Glu Leu Gly Thr Val Met Arg Ser Leu Gly Gln Asn Pro Thr Glu Ala
305                 310                 315                 320

Glu Leu Gln Asp Met Ile Asn Glu Val Asp Ala Asp Gly Asp Gly Thr
                325                 330                 335

Phe Asp Phe Pro Glu Phe Leu Thr Met Met Ala Arg Lys Met Ser Tyr
            340                 345                 350

Arg Asp Thr Glu Glu Ile Arg Glu Ala Phe Arg Val Phe Asp Lys
        355                 360                 365

Asp Gly Asn Gly Tyr Ile Gly Ala Ala Glu Leu Arg His Val Met Thr
    370                 375                 380

Asp Leu Gly Glu Lys Leu Thr Asp Glu Glu Val Asp Glu Met Ile Arg
385                 390                 395                 400

Val Ala Asp Ile Asp Gly Asp Gly Gln Val Asn Tyr Glu Glu Phe Val
                405                 410                 415

Gln Met Met Thr Ala Lys
            420

<210> SEQ ID NO 14
<211> LENGTH: 1269
<212> TYPE: DNA
<213> ORGANISM: Artificial Sequence
<220> FEATURE:
<223> OTHER INFORMATION: R-GECO2L

<400> SEQUENCE: 14
atggtcgacg tcaagctcat ccccagcctg accactgtga tcctggtcaa gtctatgctg     60
agaaagcgtt cctttggaaa cccatttccc gtggtttccg agcggatgta ccccgaggac    120
ggcgccctga gagcgagat caagaagggg ctgaggctga aggacggcgg ccactacgcc    180
gccgaggtca agaccaccta caaggccaag aagcccgtgc agctgcccgg cgcctacatc    240
gtggacatca gttggacat cgtgtcccac aacgaggact acaccatcgt ggaacagtgc    300
gaacgcgccg agggccgcca ctccaccggc ggcatggacg agctgtacaa gggaggtaca    360
ggcgggagtc tggtgagcaa gggcgaggag ataacatgg ccatcatcaa ggagttcatg    420

```
cgcttcaagg tgcacatgga gggctccgtg aacggccacg agttcgagat cgagggcgag      480
ggcgagggcc gccctacga ggcctttcag accgctaagc tgaaggtgac caagggtggc      540
cccctgccct tcgcctggga catcctgtcc cctcagttca tgtacggctc caaggcctac      600
attaagcacc cagccgacat ccccgactac ttcaagctgt ccttccccga gggcttcagg      660
tgggagcgcg tgatgaactt cgaggacggc ggcattattc acgttaacca ggactcctcc      720
ctgcaggacg gcgtattcat ctacaaggtg aagctgcgcg gcaccaactt ccccccgac       780 ggccccgtaa tgcagaagaa gaccatgggc tgggaggccg ccgtgaccaa actgactgaa      840
gagcagatcg cagaatttaa agaggctttc tccctatttg acaaggacgg ggatgggacg      900
ataacaacca aggagctggg acggtgatgc ggtctctgg gcagaacccc cacagaagca      960
gagctgcagg acatgatcaa tgaagtagat gccgacggtg acggcacatt cgacttccct      1020
gagttcctga cgatgatggc aagaaaaatg agctacagag acaccgaaga gaaattaga      1080 gaagcgttcc gcgtgtttga taaggacggc aatggctaca tcggcgcagc agagcttcgc     1140
cacgtgatga cagaccttgg agagaagtta acagatgagg aggttgatga aatgatcagg     1200
gtagcagaca tcgatgggga tggtcaggta aactacgaag agtttgtaca aatgatgaca     1260
gcgaagtag                                                              1269
```

<210> SEQ ID NO 15
<211> LENGTH: 26
<212> TYPE: PRT
<213> ORGANISM: Artificial Sequence
<220> FEATURE:
<223> OTHER INFORMATION: ckkap-WL2

<400> SEQUENCE: 15

Val Lys His Ile Pro Ser Trp Thr Thr Val Ile Leu Val Lys Ser Met
1               5                   10                  15

Leu Arg Lys Arg Ser Phe Gly Asn Pro Phe
            20                  25

<210> SEQ ID NO 16
<211> LENGTH: 26
<212> TYPE: PRT
<213> ORGANISM: Artificial Sequence
<220> FEATURE:
<223> OTHER INFORMATION: ckkap-WL3

<400> SEQUENCE: 16

Val Lys His Ile Pro Ser Leu Thr Thr Val Ile Leu Val Lys Ser Met
1               5                   10                  15

Leu Arg Lys Arg Ser Phe Gly Asn Pro Phe
            20                  25

<210> SEQ ID NO 17
<211> LENGTH: 26
<212> TYPE: PRT
<213> ORGANISM: Artificial Sequence
<220> FEATURE:
<223> OTHER INFORMATION: ckkap-WL4

<400> SEQUENCE: 17

Val Lys His Ile Pro Ser Trp Ala Thr Val Ile Leu Val Lys Ser Met
1               5                   10                  15

Leu Arg Lys Arg Ser Phe Gly Asn Pro Phe
            20                  25

```
<210> SEQ ID NO 18
<211> LENGTH: 26
<212> TYPE: PRT
<213> ORGANISM: Artificial Sequence
<220> FEATURE:
<223> OTHER INFORMATION: ckkap-WL5

<400> SEQUENCE: 18

Val Lys Leu Ile Pro Ser Leu Ala Thr Val Ile Leu Val Lys Ser Met
1               5                   10                  15

Leu Arg Lys Arg Ser Phe Gly Asn Pro Phe
            20                  25

<210> SEQ ID NO 19
<211> LENGTH: 26
<212> TYPE: PRT
<213> ORGANISM: Artificial Sequence
<220> FEATURE:
<223> OTHER INFORMATION: ckkap-WL6

<400> SEQUENCE: 19

Val Lys Leu Ile Pro Ser Trp Ala Thr Val Ile Leu Val Lys Ser Met
1               5                   10                  15

Leu Arg Lys Arg Ser Phe Gly Asn Pro Phe
            20                  25
```